US007964403B2

(12) United States Patent
Mihaliak et al.

(10) Patent No.: US 7,964,403 B2
(45) Date of Patent: Jun. 21, 2011

(54) PREPARATION OF VACCINE MASTER CELL LINES USING RECOMBINANT PLANT SUSPENSION CULTURES

(75) Inventors: Charles A. Mihaliak, Apex, NC (US); Matthew J. Fanton, Lincoln, NE (US); Janis K. McMillen, Overland Park, KS (US)

(73) Assignee: Dow AgroSciences LLC, Indianapolis, IN (US)

( * ) Notice: Subject to any disclaimer, the term of this patent is extended or adjusted under 35 U.S.C. 154(b) by 47 days.

(21) Appl. No.: 12/475,864

(22) Filed: Jun. 1, 2009

(65) Prior Publication Data

US 2010/0009449 A1 Jan. 14, 2010

Related U.S. Application Data

(62) Division of application No. 11/585,040, filed on Oct. 23, 2006, now Pat. No. 7,553,666.

(60) Provisional application No. 60/733,702, filed on Nov. 4, 2005.

(51) Int. Cl.
*A01H 5/00* (2006.01)
*C12N 15/82* (2006.01)

(52) U.S. Cl. ........ 435/419; 800/298; 800/295; 800/288; 435/468

(58) Field of Classification Search ........................ None
See application file for complete search history.

(56) References Cited

U.S. PATENT DOCUMENTS

| | | | | |
|---|---|---|---|---|
| 5,001,060 | A | 3/1991 | Peacock et al. | |
| 5,270,200 | A | 12/1993 | Sun et al. | |
| 5,273,894 | A | 12/1993 | Strauch et al. | |
| 5,276,268 | A | 1/1994 | Strauch et al. | |
| 5,290,924 | A | 3/1994 | Last et al. | |
| 5,310,678 | A | 5/1994 | Bingham et al. | |
| 5,384,253 | A | 1/1995 | Krzyzek et al. | |
| 5,484,717 | A | 1/1996 | Zaccardi | |
| 5,573,932 | A | 11/1996 | Ellis et al. | |
| 5,637,489 | A | 6/1997 | Strauch et al. | |
| 5,654,184 | A | 8/1997 | Curtiss, III et al. | |
| 5,679,880 | A | 10/1997 | Curtiss, III et al. | |
| 5,686,079 | A | 11/1997 | Curtiss, III et al. | |
| 5,773,689 | A | 6/1998 | Thompson et al. | |
| 5,773,695 | A | 6/1998 | Thompson et al. | |
| 5,824,798 | A | 10/1998 | Tallberg et al. | |
| 5,879,903 | A | 3/1999 | Strauch et al. | |
| 5,891,665 | A | 4/1999 | Wilson | |
| 5,914,123 | A | 6/1999 | Arntzen et al. | |
| 6,034,298 | A | 3/2000 | Lam et al. | |
| 6,136,320 | A | 10/2000 | Arntzen et al. | |
| 6,140,075 | A | 10/2000 | Russell et al. | |
| 6,184,437 | B1 | 2/2001 | Sun et al. | |
| 6,194,560 | B1 | 2/2001 | Arntzen et al. | |
| 6,239,328 | B1 | 5/2001 | Thompson | |
| 6,320,101 | B1 | 11/2001 | Kaplan et al. | |
| 6,395,964 | B1 | 5/2002 | Arntzen et al. | |
| 7,132,291 | B2 * | 11/2006 | Cardineau et al. | 435/468 |
| 2004/0166121 | A1 | 8/2004 | Arntzen et al. | |
| 2004/0268442 | A1 | 12/2004 | Miller et al. | |
| 2005/0048074 | A1 | 3/2005 | Cardineau et al. | |
| 2006/0222664 | A1 | 10/2006 | Miller et al. | |

FOREIGN PATENT DOCUMENTS

| | | |
|---|---|---|
| EP | 0348947 | 1/1990 |
| WO | WO 91/09957 | 7/1991 |
| WO | WO 97/27207 | 7/1997 |
| WO | WO 97/48819 | 12/1997 |
| WO | WO 00/37609 | 6/2000 |
| WO | WO 2004/098530 | 11/2004 |
| WO | WO 2004/098533 | 11/2004 |

OTHER PUBLICATIONS

Etienne et al. Biotechnological applications for the improvement of coffee (Coffea Arabica L.). (2002) In Vitro Cell. Dev. Biol.-Plant; vol. 38, pp. 129-138.*

Huang et al. Expression of recombinant influenze virus antigens in transgenic plants as an oral vaccine for poultry. (1999) FASEB Journal; vol. 13; abstract # 245.19.*

Garcia, M. Hemagglutinin (influenza A virus). (1998) GenBank Accession AAC58998.1; p. 1 of 1.*

Russell et al. Physical trauma and tungsten toxicity reduce the efficiency of biolistic transformation. (1992) Plant Phys.; vol. 98, pp. 1050-1056.*

Gabridge, M. G. et al. "Culivation of Mycoplasmas in a Modified Tissue Culture Medium" *Applied and Environmental Microbiology*, Jun. 1976, pp. 986-989, vol. 31, No. 6.

Munoz, G. et al. "Conditions for Growing *Mycoplasma canadense and Mycoplasma verecundum* in a Serum-Free Medium" *Applied and Environmental Microbiology*, Jul. 1990, pp. 2259-2261, vol. 56, No. 7.

Taylor-Robinson, D. et al. "The prolonged persistence of mycoplasmas in culture" *J. Med. Microbiol.*, 1987, pp. 89-92, vol. 23.

GenBank Accession No. AF077761, Mar. 23, 1999, pp. 1-8.

GenBank Accession No. X00493, Apr. 18, 2005, pp. 1-16.

Etienne, H. et al., "Biotechnological Applications for the Improvement of Coffee (*Coffea arabica L.*)", In Vitro *Cell. Dev. Biol.—Plant*, Mar.-Apr. 2002, pp. 129-138, vol. 38.

Russell, J.A. et al., "Physical Trauma and Tungsten Toxicity Reduce the Efficiency of Biolistic Transformation", *Plant Physiol.*, 1992, pp. 1050-1056, vol. 98.

Liao, C. H. et al. "Presence of spiroplasma-inhibitory substances in plant tissue extracts" *Canadian Journal of Microbiology*, 1980, pp. 807-811, vol. 26, No. 7, XP-009114017.

Ogata, M. et al. "Investigation on Growth Media for Mycoplasma: Evaluation of Infusions, Peptones, Sera, Yeast Extracts and Other Supplements" *Japanese Journal of Veterinary Science*, 1967, pp. 259-271, vol. 29, No. 5, XP-009114016.

* cited by examiner

*Primary Examiner* — Cathy Kingdon Worley
(74) *Attorney, Agent, or Firm* — Ronald S. Maciak; Saliwanchik, Lloyd & Eisenschenk

(57) ABSTRACT

The subject invention provides a plant cell culture for producing proteinaceous agents comprising a plant cell line stably transformed to express a transgene encoding a proteinaceous agent and a growth medium which supports the growth of said plant cell culture but which does not support the growth of Mycoplasmataceae and contains no materials of animal origin. The plant cell line is capable of being continuously passaged such that consistent transgene expression is maintained during passaging. The plant cell line is also capable of being cryopreserved such that consistent transgene expression is recovered upon recovery from cryopreservation.

6 Claims, 15 Drawing Sheets

```
NcoI
cc ATG GAC AGA GCA GTT TCA CAA GTG GCC CTA GAG AAT GAT GAG AGG GAA GCC
   > M  D   R   A   V   S   Q   V   A   L   E   N   D   E   R   E   A
AAG AAT ACC TGG AGG CTT ATA TTC AGA ATA GCC ATC TTA TTC CTT ACT GTG GTC
 K   N   T   W   R   L   I   F   R   I   A   I   L   F   L   T   V   V
                                        BseRI
                     BseRI cut site
ACC CTA GCA ATC TCT GTT GCA TCC CTC CTC TAT TCT ATG GGA GCA AGC ACC CCC
 T   L   A   I   S   V   A > S   L   L   Y   S   M   G   A   S   T   P
TCA GAC TTG GTG GGC ATA CCC ACA AGA ATC TCT AGG GCA GAA GAA AAA ATC ACC
 S   D   L   V   G   I   P   T   R   I   S   R   A   E   E   K   I   T
AGT ACC CTT GGC TCC AAC CAA GAT GTT GTG GAC AGA ATC TAC AAA CAG GTG GCA
 S   T   L   G   S   N   Q   D   V   V   D   R   I   Y   K   Q   V   A
CTT GAA AGT CCA CTT GCA TTA CTC AAC ACA GAG ACT ACC ATC ATG AAT GCA ATT
 L   E   S   P   L   A   L   L   N   T   E   T   T   I   M   N   A   I
ACC AGC CTA TCC TAT CAA ATT AAT GGG GCT GCC AAC AAT TCA GGT TGG GGA GCC
 T   S   L   S   Y   Q   I   N   G   A   A   N   N   S   G   W   G   A
CCA ATT CAT GAT CCA GAC TAT ATT GGA GGT ATT GGC AAA GAG CTT ATT GTA GAT
 P   I   H   D   P   D   Y   I   G   G   I   G   K   E   L   I   V   D
GAT GCT TCA GAT GTT ACA TCT TTC TAT CCT TCA GCT TTC CAG GAA CAC CTG AAT
 D   A   S   D   V   T   S   F   Y   P   S   A   F   Q   E   H   L   N
TTC ATT CCT GCA CCC ACA ACT GGG AGT GGG TGC ACT AGA ATA CCC TCA TTT GAC
 F   I   P   A   P   T   T   G   S   G   C   T   R   I   P   S   F   D
ATG AGT GCT ACA CAC TAC TGC TAC ACA CAT AAT GTT ATT CTC TCT GGC TGT AGG
 M   S   A   T   H   Y   C   Y   T   H   N   V   I   L   S   G   C   R
GAC CAC TCT CAC TCT TAT CAA TAC TTA GCT CTT GGA GTT CTC AGA ACA TCT GCT
 D   H   S   H   S   Y   Q   Y   L   A   L   G   V   L   R   T   S   A
ACT GGT AGA GTC TTT TTC TCA ACT CTT AGG AGT ATC AAC CTA GAT GAT ACA CAA
 T   G   R   V   F   F   S   T   L   R   S   I   N   L   D   D   T   Q
AAT AGG AAA AGT TGC TCT GTA TCT GCT ACA CCT TTG GGC TGT GAT ATG CTA TGC
 N   R   K   S   C   S   V   S   A   T   P   L   G   C   D   M   L   C
AGT AAA GTA ACA GAA ACT GAA GAA GAG GAC TAT AAT TCT GCT GTC CCT ACA AGG
 S   K   V   T   E   T   E   E   E   D   Y   N   S   A   V   P   T   R
ATG GTG CAT GGC AGA TTG GGT TTT GAT GGT CAA TAT CAT GAA AAA GAT TTG GAT
 M   V   H   G   R   L   G   F   D   G   Q   Y   H   E   K   D   L   D
GTC ACT ACA TTG TTT GGG GAT TGG GTA GCT AAT TAC CCA GGA GTT GGA GGT GGT
 V   T   T   L   F   G   D   W   V   A   N   Y   P   G   V   G   G   G
AGC TTC ATT GAC TCC AGA GTC TGG TTC TCT GTC TAT GGT GGT TTA AAA CCT AAC
 S   F   I   D   S   R   V   W   F   S   V   Y   G   G   L   K   P   N
AGT CCT AGT GAT ACT GTG CAA GAG GGA AAG TAT GTT ATC TAC AAG AGG TAT AAT
 S   P   S   D   T   V   Q   E   G   K   Y   V   I   Y   K   R   Y   N
GAT ACT TGT CCT GAT GAA CAG GAT TAC CAG ATT AGG ATG GCT AAG TCA TCA TAC
 D   T   C   P   D   E   Q   D   Y   Q   I   R   M   A   K   S   S   Y
AAA CCA GGA AGA TTT GGA GGT AAG AGG ATA CAA CAA GCT ATT TTG AGT ATT AAG
 K   P   G   R   F   G   G   K   R   I   Q   Q   A   I   L   S   I   K
GTT AGC ACA TCA TTG GGA GAG GAC CCA GTC CTT ACT GTT CCA CCA AAC ACT GTA
 V   S   T   S   L   G   E   D   P   V   L   T   V   P   P   N   T   V
ACA CTC ATG GGA GCT GAG GGA AGG ATT TTA ACT GTT GGT ACT AGC CAT TTT CTT
 T   L   M   G   A   E   G   R   I   L   T   V   G   T   S   H   F   L
TAT CAG AGA GGA AGT TCC TAT TTT AGC CCA GCA TTA CTG TAT CCA ATG ACT GTG
 Y   Q   R   G   S   S   Y   F   S   P   A   L   L   Y   P   M   T   V
AGC AAC AAG ACA GCT ACA TTA CAT TCA CCA TAT ACT TTT AAT GCT TTT ACA AGA
 S   N   K   T   A   T   L   H   S   P   Y   T   F   N   A   F   T   R
```

FIG. 1A

```
CCT GGA TCA ATT CCT TGC CAG GCT TCA GCT AGA TGT CCA AAT TCA TGT GTG ACT
 P   G   S   I   P   C   Q   A   S   A   R   C   P   N   S   C   V   T
GGA GTT TAC ACT GAT CCT TAC CCT TTG ATA TTT TAC AGA AAT CAT ACC TTG AGA
 G   V   Y   T   D   P   Y   P   L   I   F   Y   R   N   H   T   L   R
GGG GTT TTT GGA ACA ATG TTG GAT GGT GTT CAA GCT AGG CTC AAT CCT GCC TCT
 G   V   F   G   T   M   L   D   G   V   Q   A   R   L   N   P   A   S
GCT GTT TTT GAT TCT ACA TCA AGA TCA AGA ATA ACC AGG GTT TCC TCT AGT TCC
 A   V   F   D   S   T   S   R   S   R   I   T   R   V   S   S   S   S
ACT AAG GCA GCA TAT ACT ACC TCC ACA TGT TTC AAA GTT GTA AAG ACT AAC AAA
 T   K   A   A   Y   T   T   S   T   C   F   K   V   V   K   T   N   K
                              BglII
ACT TAT TGT CTG AGC ATA GCT GAG ATC TCT AAC ACT CTT TTT GGG GAG TTC AGA
 T   Y   C   L   S   I   A   E   I   S   N   T   L   F   G   E   F   R
                                                                   BglII
ATT GTT CCA CTT TTG GTG GAA ATT CTG AAG GAT GAT GGT GTA AGG GAA GCA AGA
 I   V   P   L   L   V   E   I   L   K   D   D   G   V   R   E   A   R
                    KpnI
    BbsI cut site          SacI
          BbsI
TCT GGT TAA gtcttcaggt accgagctc
 S   G   •
```

FIG. 1B

```
   1 gaccaaatct gcatcggtta tcatgcaaac aattcaacaa aacaagttga cacaatcatg
  61 gagaagaatg tgacggtcac acatgctcaa gatatactgg aaaaagagca caacgggaaa
 121 ctctgcagtc tcaaaggagt gaggcccctc attctgaagg attgcagtgt ggctggatgg
 181 cttcttggga acccaatgtg tgatgagttc ctaaatgtac cggaatggtc atatattgta
 241 gagaaggaca atccaaccaa tggcttatgt tatccgggag acttcaatga ttatgaagaa
 301 ctgaagtatt taatgagcaa cacaaaccat tttgagaaaa ttcaaataat ccctaggaac
 361 tcttggtcca atcatgatgc ctcatcagga gtgagctcag catgcccata caatggtagg
 421 tcttcctttt tcaggagtgt ggtgtggttg atcaagaaga gtaatgtata cccaacaata
 481 aagaggacct acaataacac caatgtagag gaccttctga tattgtgggg aatccatcac
 541 cctaatgatg cagcggaaca aacggaactc tatcagaact cgaacactta tgtgtctgta
 601 ggaacatcaa cactaaatca gaggtcaatt ccagaaatag ctaccaggcc caaagtgaat
 661 ggacaaagtg gaagaataga atttttctgg acaatactaa ggccgaacga tgcaatcagc
 721 tttgaaagta atgggaactt tatagctcct gaatatgcat acaagatagt taaaaaggga
 781 gattcagcaa tcatgagaag cgaactggag tatggcaact gtgataccaa atgtcagacc
 841 ccagtgggtg ctataaattc cagtatgcct tttcacaatg ttcatcccct taccattgga
 901 gagtgtccca aatatgtcaa atcagataaa ctggtccttg caacaggact gaggaacgtg
 961 cctcagagag aaacaagagg tctgtttgga gcaatagcag gattcataga agggggatgg
1021 caaggaatgg tagatggatg gtatggttac catcatagca acgagcaggg aagtggatat
1081 gctgcagaca aagagtccac tcagaaagca atcgacggga tcaccaataa agtcaactca
1141 atcattgaca aaatgaacac tcaattcgaa gccgttggga aagaattcaa caacttagaa
1201 aggagaatag aaaatttgaa taagaaaatg gaagatggat ttctagatgt atggacttac
1261 aatgcagaac ttctggtgct catggaaaat gaaagaactc tggatttcca tgattcatat
1321 gtcaagaacc tatacgataa ggtccgactc cagctgagag ataatgcaaa agaattgggc
1381 aatgggtgtt tggagttctc ccacaaatgt gacaatgaat gcatggaaag tgtgagaaac
1441 ggaacgtatg actatccaca atactcagaa gaatcaaggc tgaacagaga ggaaatagat
1501 ggagtcaaat tggagtcaat gggcacctat cagatactat caatttactc aacagtggcg
1561 agttccctag cactggcaat catggtagct ggtctgtctt tttggatgtg ctccaatgga
1621 tcattgcaat gcagaatttg catctag
                                                  (SEQ ID NO:3)
```

```
                     DQICIGYHANNSTKQVDTIMEKNVTVTHAQDILEKEHNGKLCSL
KGVRPLILKDCSVAGWLLGNPMCDEFLNVPEWSYIVEKDNPTNGLCYPGDFNDYEELK
YLMSNTNHFEKIQIIPRNSWSNHDASSGVSSACPYNGRSSFFRSVVWLIKKSNVYPTI
KRTYNNTNVEDLLILWGIHHPNDAAEQTELYQNSNTYVSVGTSTLNQRSIPEIATRPK
VNGQSGRIEFFWTILRPNDAISFESNGNFIAPEYAYKIVKKGDSAIMRSELEYGNCDT
KCQTPVGAINSSMPFHNVHPLTIGECPKYVKSDKLVLATGLRNVPQRETRGLFGAIAG
FIEGGWQGMVDGWYGYHHSNEQGSGYAADKESTQKAIDGITNKVNSIIDKMNTQFEAV
GKEFNNLERRIENLNKKMEDGFLDVWTYNAELLVLMENERTLDFHDSYVKNLYDKVRL
QLRDNAKELGNGCLEFSHKCDNECMESVRNGTYDYPQYSEESRLNREEIDGVKLESMG
TYQILSIYSTVASSLALAIMVAGLSFWMCSNGSLQCRICI
                                                  (SEQ ID NO:4)
```

FIG. 10 atgaccaacctccaagatcaaactcaacagattgttcccttcatacgcagccttctcatgccaaccactggacctgct
tccattcctgatgacaccttggagaagcacactctccgctctgagacctcaacctacaacttgactgttggtgacact
ggctctgggttgattgtctttttccctgggttccctggctccattgtgggtgctcactacacattgcagtccaatggc
aactacaagtttgatcaaatgctcttgactgcccagaatcttccagcctcctacaactattgccgtcttgtgtctcgc
tccctcacagtgaggtcctcaacactccctggtggagtgtatgcactcaatggcaccatcaacgcagtgactttccaa
ggaagcctttcagaattgactgatgtgagctacaatgggttgatgtctgcaacagccaacatcaatgacaagattggg
aatgtccttgttggagaaggagtcaccgtcctctcactcccaacatcctatgatcttggctatgtgagacttggtgat
cccattcctgccataggacttgatcccaaaatggttgccacatgtgacagctctgatcgtccaagggtttacaccatc
acagcagctgatgactaccaattctcctcacagtaccaagctggtggagtcaccatcacactcttctcagccaacata
gatgccatcacaagcctcagcattggtggagaacttgtctttcagacatctgtccaaggctcatccttggtgccacc
atctacttgattggctttgatggcactgctgtcatcaccagagcagtggctgcagacaatggctcacagctggcact
gacaacctcatgccattcaacattgtgattcccacctctgagatcacccagccaatcacttccatcaagttggagata
gtgacctcaaagtccggtggacaagctggtgatcagatgtcctggtctgcatctgggagcttggctgtgaccattcat
ggtggcaactaccccggagccctcagacctgtgactttggttgcctatgaacgcgttgcaactggctctgttgtcact
gttgctggtgtcagcaactttgagttgatcccaaatcctgaacttgcaaagaacttggtcacagagtatggaaggttt
gaccctggtgccatgaactacacaaaattgatcctctcagagagggacagacttggcatcaagactgtttggccaacc
agagagtacactgacttccgcgagtacttcatggaggttgctgacctcaacagccctctcaagatagctggagccttt
ggtttcaaagacatcataagggctattcgtcgcatcgctgtt (SEQ ID NO:10)

FIG. 14

PREPARATION OF VACCINE MASTER CELL LINES USING RECOMBINANT PLANT SUSPENSION CULTURES

CROSS-REFERENCE TO RELATED APPLICATIONS

This application is a divisional of U.S. patent application Ser. No. 11/585,040, filed Oct. 23, 2006, now U.S. Pat. No 7,553,666, which claims the benefit of U.S. provisional application Ser. No. 60/733,702, filed Nov. 4, 2005. Each of these applications is incorporated herein by reference in its entirety, including all tables, figures and polynucleotide and polypeptide sequence listings.

FIELD OF INVENTION

The present invention generally relates to the fields of plant cell culture and protein production in plant cell cultures. In particular the invention relates to a universal production system and plant cell lines capable of producing a wide variety of simple and complex proteins for use as therapeutic agents and vaccines.

BACKGROUND OF THE INVENTION

Recombinant DNA technology has provided substantial improvements in the safety, quality, efficacy and cost of pharmaceutical and veterinary medicaments including vaccines. Plant produced mucosal vaccines were invented by Curtiss & Cardineau. See U.S. Pat. Nos. 5,654,184; 5,679,880 and 5,686,079 herein incorporated by reference. Others have described transgenic plants expressing immunoprotective antigens and methods for production including Arntzen, Mason and Lam. See U.S. Pat. Nos. 5,484,717; 5,914,123; 6,034,298; 6,136,320; 6,194,560; and 6,395,964 herein incorporated by reference in their entireties.

Plant cell production using cell culture in defined media avoids the need for animal-sourced components in growth media essentially eliminating the risk of transmitting pathogenic contaminants from the production process. Plants cells are capable of posttranslational glycosylation, and plant cell growth media is generally less expensive, easier to handle and prepare as compared to conventional growth media presently used in the manufacture of vaccines.

Vaccine antigens and proteins of pharmacological or relevant biological activity produced in plant systems offer a number of advantages over conventional production systems. Plant derived subunit proteins cannot revert to virulence (a feature of live conventionally or recombinantly produced live vectored vaccines). Subunit proteins produced from conventional manufacturing methods may be difficult to produce and purify due to protein instability and biochemical extraction issues, and subunit vaccine components that require glycosylation will not be glycosylated when produced in prokaryotes.

Plants provide unique benefits that are difficult to derive from any single conventional or mammalian derived recombinant DNA systems. Traditionally, subunit vaccines or proteinaceous agents are: 1) difficult to purify from recombinant or conventional sources because of low yields making their production prohibitive; 2) unstable due to the proteolysis, pH, or solvents used during purification; 3) less efficacious because they are not native, or the purification process denatures key epitopes; and 4) hampered with extraneous materials of biological origin when produced in mammalian systems (mentioned above).

"Master cell line" principles for biopharmaceutical production utilize live organisms as part of the manufacturing procedure and rely on some basic tenets: 1) a single culture of defined origin and passage history is preserved with defined characteristics of cell phenotype and desired manufacturing features; 2) preservation, typically cryopreservation, is long lasting (spanning several years or more); 3) the cell can be recovered, expanded, passaged indefinitely into "working seed" and subjected to another period of cryopreservation (a principle that requires robustness of the cell; and 4) the cell does not lose the defined characteristics of cell phenotype and desired manufacturing features found prior to the initial cryostate after a defined number of passages.

Thus, the art is in need of plant cells and plant cell cultures that provide for the long term growth, re-cryopreservation, and stability of biomanufacturing target components under master seed principles.

SUMMARY OF THE INVENTION

The invention is provides plant cell cultures and methods of culturing and storing plant cells for the production of proteinaceous agents suitable for regulatory compliance and GMP (Good Manufacturing Practices) manufacturing practices. In certain aspects of the invention, transgenic cell cultures are used to express simple or complex biopharmaceutical protein and peptide agents useful in vaccine, industrial, pharmaceutical and pharmacological preparations. Other aspects of the invention provide a plant-cell-produced vaccine production system. Furthermore, the plant master cell lines set forth herein display stability and robustness sufficient to meet regulatory requirements.

BRIEF DESCRIPTION OF THE FIGURES

FIGS. 1A and 1B (SEQ ID NOs:1 and 2). The plant optimized coding sequence and protein sequence of the HN gene of NDV strain "Lasota".

FIG. 10 (SEQ ID NOs:3 and 4). The DNA and protein sequences of the HA gene of AIV A/turkey/Wisconsin/68 (H5N9).

FIG. 14 (SEQ ID NO:10). The DNA sequence of VP2 gene of IBDV Infectious Bursal Disease (IBD) virus, very virulent strain Ehime 91.

SUMMARY OF THE SEQUENCES

Figure 2:
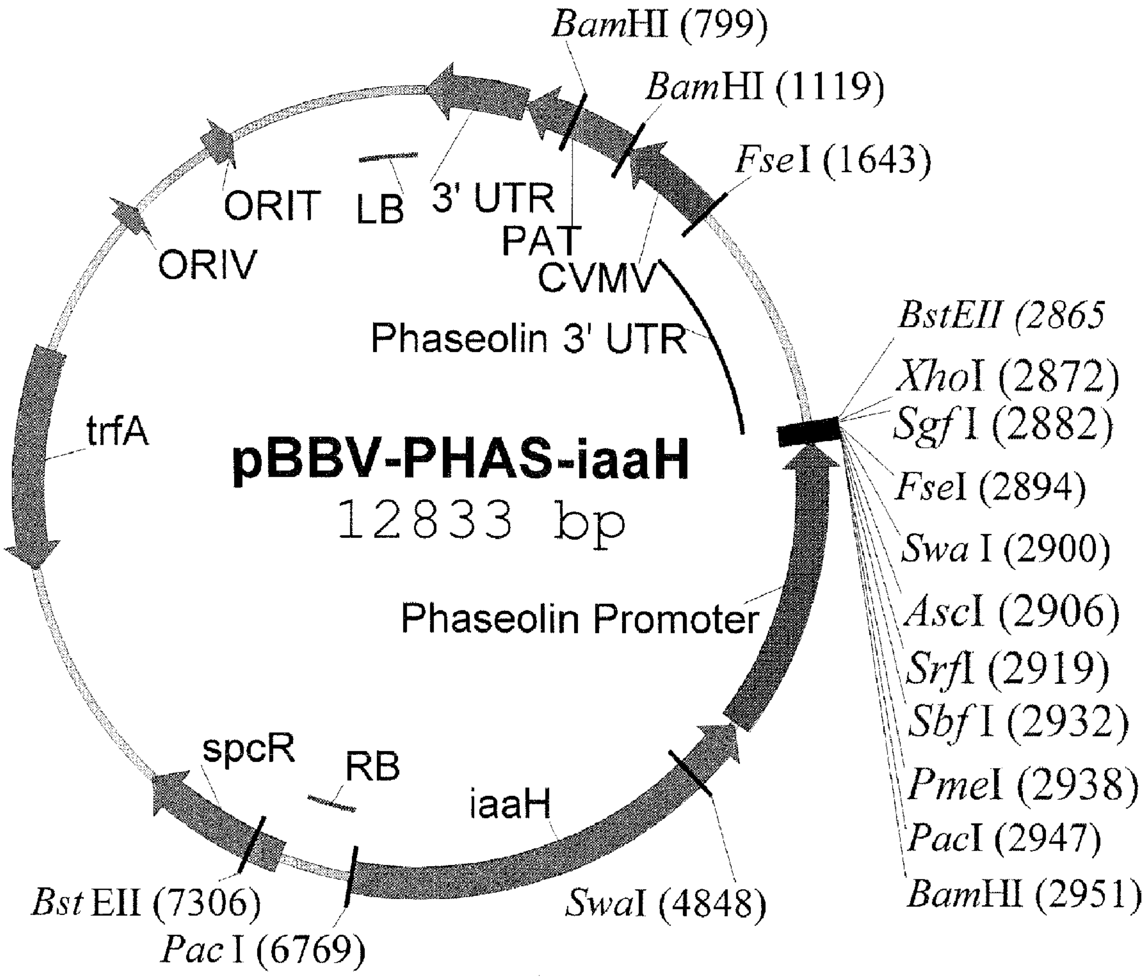
FIG. 2. Map of pBBV-PHAS-iaaH that contains the plant selectable marker PAT (phosphinothricin acetyl transferase) driven by the constitutive CsVMV (cassava vein mosaic virus) promoter and terminated by the MAS 3' (mannopine synthase) element. LB and RB (left and right T-DNA border) elements from *Agrobacterium* that delineate the boundaries of the DNA that is integrated into the plant genome.

SEQ ID NOs:1 and 2, shown in FIGS. 1A and 1B, are the plant optimized coding sequence and protein sequence of the FIN gene of NDV strain "Lasota".

SEQ ID NOs:3 and 4, shown in FIG. 10, are the DNA and protein sequences of the HA gene of AIV A/turkey/Wisconsin/68 (H5N9).

SEQ ID NO:5 is a PCR primer used to end-tailor the CsVMV promoter on pCP!H.

SEQ ID NO:6 is a PCR primer used to end-tailor the CsVMV promoter on pCP!H.

SEQ ID NO:7 is a mutagenic primer used to create a Nco I site.

SEQ ID NO:8 is forward primer complimentary to the 5' region.

SEQ ID NO:9 is a mutagenic primer used to create a XhoI I site.

SEQ ID NO:10 shown in FIG. 14 is the DNA sequence of VP2 gene of infectious bursal disease virus.

SEQ ID NO:11 is a plant-optimized DNA sequence encoding a variation of E/91 VP2 (1425 bases). The coding region for F/91 plant-optimized VP2 comprises bases 16 to 1383 (1371 bases). Six frame stops are found at bases 1384 to 1425.

SEQ ID NO:12 comprises the sequence of the E/91 VP2 protein encoded by the plant-optimized version of the E/91 VP2 coding region (SEQ ID NO:11).

SEQ ID NO:13 is the DNA sequence encoding translation termination ("Stop") codons in six reading frames. The sequence was used to terminate translation of inadvertent open reading frames following DNA integration during transformation and includes Sac I BstE II, and Bgl II restriction enzyme recognition sites (Tsukamoto K., Kojima, C., Komori, Y., Tanimura, N., Mase, M., and Yamaguchi, S. (1999) Protection of chickens against very virulent infectious bursal disease virus (IBDV) and Marek's disease virus (MDV) with a recombinant MDV expressing IBDV VP2. Virol. 257: 352-362.)

DETAILED DESCRIPTION OF THE INVENTION

Certain aspects of the subject application provide a plant cell culture for producing proteinaceous agents comprising a plant cell line stably transformed to express a transgene encoding a proteinaceous agent and a growth medium which supports the growth of said plant cell culture but which does not support the growth of Mycoplasmataceae and contains no materials of animal origin. The plant cell line is capable of being continuously passaged such that consistent transgene expression is maintained during passaging and is capable of being cryopreserved such that consistent transgene expression is recovered upon recovery from cryopreservation.

Other aspects of the subject application provide a plant cell culture producing a proteinaceous vaccine or therapeutic agent having one or more of the following characteristics: a) a lack of animal products in the culture/growth medium; b) free of detectable levels of plant secondary metabolites (e.g., nicotine metabolites); or c) free of detectable levels of mycoplasma, viruses, bacteria or fungi. Thus, the plant cell cultures provided by the subject invention can have any one, two, or all three of the characteristics set forth in this paragraph (e.g., characteristic a); or characteristic b); or characteristic c); or characteristics a) and b); or characteristics a) and c); or characteristics b) and c); or characteristics a) and b) and c)).

The subject invention also provides a stably transformed plant based vaccine production system that comprises one or more of the following characteristics: a) selection and establishment of a recombinant plant cell culture master cell line that expresses a proteinaceous agent, can be permanently stored, and can serve as the source of all other passages from which all other seeds and passages are derived; b) ability to create working seed (a stored source derived from the master cell line and used to prepare production seeds) and production seed (the recombinant cells at a specified ranges of passage levels which are used without further propagation to initiate production of a plant-made proteinaceous agent); c) proteinaceous agents can be produced by growing stably transformed plant cells in a bioreactor in the absence (without the use of) products of animal origin (e.g., serums of mammalian origin such as horse, fetal calf, etc.); d) safe for administration to animals via cutaneous, intramuscular, intranasal, or oral delivery; e) free of detectable levels plant secondary metabolites (e.g., polycyclic aromatic hydrocarbons and nitrosamines, including anatabine, anabasine, benzo(a)pyrene, nicotine and nornicotine; f) free of mycoplasma, viruses, fungi, or bacteria; g) produces a proteinaceous agent or vaccine that is stable as a lyophilized powder for long periods of up to several years, preferably 1 to 10 years, and more preferably 1 to 5 years, under ambient, refrigerated or frozen conditions; h) assembled proteinaceous agent (vaccine) (e.g., vaccine antigen or proteinaceous agent in combination with adjuvants) is stable for months under refrigerated conditions; i) the system can be used in a process that can be performed in contained conditions and without the need to regenerate fertile plants; j) the system provides master cell lines that can be thawed with high rates of recovery (e.g., rates of recovery of up to 100% or rates of recovery that are at least or greater than 90, 91, 92, 93, 94. 95, 96, 97, 98, or 99% recovery); k) provides for the preparation and recovery of cryopreserved working seed with high rates of recovery (e.g., rates of recovery of up to 100% or rates of recovery that are at least or greater than 90, 91, 92, 93, 94. 95, 96, 97, 98, or 99% recovery) from cryopreserved master cell lines; 1) resulting proteinaceous agent or vaccine can be formulated into conventional vaccine assemblies (proteinaceous agent/vaccine combined with known adjuvants) or novel vaccine assemblies (e.g., cell pastes) and administered to provide serological conversion and/or disease protection in vaccinated individual); m) provides a conventional or novel vaccine assembly having 2,4-D levels below established tolerance levels for livestock or poultry; n) is scalable to commercial manufacturing processes (e.g., the system or cells can be cultured in vessels ranging from shake flasks to bioreactors ranging from 10 liters to 100,000 liters; preferably from 100 liters to 1,000 or 5,000 or 10,000); o) produces plant cell line that are stably transformed; and/or p) can be used for the preparation of master and working references (a reference material whose potency is correlated directly or indirectly in the host animal (e.g., biological activity of a cytokine or antigenicity/immunogenicity of a vaccine antigen). Certain aspects of the invention provide a plant-made vaccine production system having all of the above-identified characteristics.

As used herein, the phrase “free of detectable levels” of a secondary metabolytes is to be understood to mean that the substance being assayed cannot be detected using standard techniques such as GC/MS and LC/MS techniques. Detection limits for these techniques are 100 ng/ml. The term “free of mycoplasma, viruses, fungi and bacteria” means there are no such organism present as determined by biological testing such as is described in Example 5 herein.

2,4-D tolerance levels for poultry: A conservative estimate of 2,4-D residues resulting from vaccination for prevention of an avian disease virus is an inconsequential 0.007% of the current EPA established tolerance for 2,4-D in eggs. The current EPA tolerance established for 2,4-D in poultry is 0.05 mg/kg or 50 μg/kg. A conservative estimate of 2,4-D residues resulting from vaccination for the prevention of an avian virus is an inconsequential 0.00079% of the current EPA established tolerance for 2,4-D in poultry tissue.

The phrases “stably transformed”, “plant cell line stably transformed” or “stably transformed plant based vaccine production system” or “consistent transgene expression” provide for plant cell lines or plant based vaccine production systems that grow vigorously, produce the biologically and immunologically active antigen for over one hundred (100) passages, and, optionally, contain a recombinant insert (genetic event) that remains unchanged over time and passage number as demonstrated based on genetic analyses such as Southern blots, PCR, or AFLP resulting in no significant changes in phenotype growth rate, or transgene expression levels.

Plant cell cultures as set forth in this application can contain transformed plant cell lines derived from a lower plant, a dicotyledonous plant or a monocotyledonous plant. Non-limiting examples of dicotyledonous plants from which the transformed cell lines can be derived are tomato, potato, sweet potato, cassava, legumes including alfalfa and soybean, carrot, strawberry, lettuce, oak, maple, walnut, rose, mint, sunflower, safflower, cotton, tobacco, squash, daisy, canola or cactus. Certain aspects of the invention utilize tobacco cells lines such as NT-1 or BY-2. Where the transformed plant cell line is derived from a monocotyledonous plant, plants such as wheat, turf, turf grass, cereal, maize or corn, rice, oat, wheat, barley, sorghum, orchid, iris, lily, onion, banana, sugarcane, sorghum, or palm can be used to establish the plant cell line. Additionally, cell lines can be established from lower plants such as ferns, gymnosperms, conifers, horsetails, club mosses, liver warts, hornworts, mosses, red algaes, brown algaes, gametophytes, sporophytes of pteridophytes, or green algae. A preferred group of plant cell cultures useful in the present invention is plant cell cultures derived from corn, rice or tobacco plants.

Proteinaceous pharmaceutical or vaccine agents include, but are not limited to enzymes, toxins, cell receptors, ligands, viral or bacterial proteins or antigens, signal transducing agents, cytokines, or other therapeutical proteins expressed in transgenic plant cell culture. Polynucleotide sequences encoding such proteinaceous pharmaceutical or vaccine agents can be obtained from commercial databases such as EMBL, SWISSPROT, or the NCBI database. A proteinaceous agent can also be one or more protein (antigen) from particular pathogenic viruses including, but not limited to the HA (hemagglutinin) protein of AIV (Avian Influenza Virus), a type 1 glycoprotein; the HN (hemagglutinin/neuraminidase) protein of avian NDV (Newcastle Disease Virus) a type 2 glycoprotein, (see U.S. Pat. No. 5,310,678, herein incorporated by reference); a structural protein, VP2, of infectious bursa disease virus (IBDV); an enzyme ADP ribosyl transferase (LT-A subunit of heat labile toxin of *E. coli*); a bacterial toxin LT of *E. coli* made up of two subunits, human viruses including but not limited to poliovirus, human rhinovirus (HRV), hepatitis A virus (HAV), immunodeficiency virus (HIV), human papillomavirus (HPV), herpes simplex virus (HSV), picornaviruses such as foot-and-mouth disease virus (FMDV), flaviviruses such Dengue and West Nile viruses and respiratory syncytial virus (RSV). Typically proteinaceous agents produced in transgenic plant cell cultures are equivalent in functional or structural activity to the same proteins isolated from natural sources. Non-limiting examples of viral antigens are also set forth in SEQ ID NOs:1, 2, 3, 4, 11, and 12.

Vaccination and vaccinating is defined as a means for providing protection or inducing seroconversion (e.g., the production of antibodies) against a pathogen by inoculating a host with an immunogenic preparation containing a proteinaceous agent such that the host immune system is stimulated and prevents or attenuates subsequent unwanted pathology associated with the host reactions to subsequent exposures of the pathogen.

A vaccine is a composition used to vaccinate an animal, including a human, that contains at least one proteinaceous agent that induces the stimulation of the host immune system and prevents or attenuates subsequent unwanted pathology associated with the host reactions to subsequent exposures of the pathogen immunoprotective antigenic substances.

A pathogenic organism is a *bacterium*, virus, fungus, or protozoan that causes a disease or induced/controlled physiologic condition in an animal or host that it has infected.

For purposes of this specification, an adjuvant is a substance that accentuates, increases, moderates or enhances the immune response to an immunogen or antigen. Adjuvants typically enhance both the humor and cellular immune response but an increased response to either in the absence of the other qualifies to define an adjuvant. Moreover, adjuvants and their uses are well known to immunologists and are typically employed to enhance the immune response when doses of immunogen are limited, when the immunogen is poorly immunogenic, or when the route of administration is sub-optimal. Thus the term “adjuvating amount” is that quantity of adjuvant capable of enhancing the immune response to a given immunogen or antigen. The mass that equals an ‘adjuvating amount’ will vary and is dependant on a variety of factors including, but not limited to, the characteristics of the immunogen, the quantity of immunogen administered, the host species, the route of administration, and the protocol for administering the immunogen. The “adjuvating amount” can readily be quantified by routine experimentation given a particular set of circumstances. This is well within the ordinarily skilled artisan’s purview and typically employs the use of routine dose response determinations to varying amounts of administered immunogen and adjuvant. Responses are measured by determining serum antibody titers or cell-mediated responses raised to the immunogen using enzyme linked immunosorbant assays, radio immune assays, hemagglutination assays and the like.

An effective dosage is an amount necessary to induce an immune response in a human or animal sufficient for the human or animal to effectively resist a challenge mounted by pathogenic agent or to respond to a physiological requirement of the animal such as an autoimmune antigen to diabetes. The dosages administered to such human or animal will be determined by a physician, veterinarian, or trained scientist in the light of the relevant circumstances including the particular immunoprotective particle or combination of particles, the condition of the human or animal, and the chosen route of administration. Generally, effective dosages range from about 1 ng to about 0.5 mg, and preferably from about 1 ug to about 50 ug. For Newcastle Disease Virus (HN antigen) in poultry effective dosages range from about 0.5 ug to about 50 ug, preferably from about 2.5 ug to about 5 ug via the SQ route. Via the IN/ocular mucosal route effective dosages for HN in poultry range from about 0.5 ug to about 50 ug, preferably from about 5 ug to about 25 ug, and more preferably from about 10 ug to about 12 ug. For Avian Influenza Virus (HA antigen) effective dosages range from about 0.5 ug to about 50 ug, preferably from about 1 ug to about 30 ug, and more preferably from about 24 ug to about 26 ug via the IN/ocular route and preferably from about 1 ug to about 5 ug via the SQ route. For Infectious Bursal Disease (VP2 antigen) in poultry effective dosages range from 0.5 ug to about 50 ug, preferably from about 5 ug to about 25 ug, and more preferably from about 5 ug to about 20 ug via the SQ route. For LT antigen effective oral dosages range from about 50 ng to about 250 ng, preferably from about 100 ng to about 200 ng. For LT antigen effective SQ or IN/ocular dosages range from about 50 ng to about 100 ug; preferably from about 1 ug to about 50 ug and more preferably from about 2 ug to about 10 ug. The dosage ranges presented herein are not intended to limit the scope of the invention in any way and are presented as general guidance for the skilled practitioner.

Transgenic plant is herein defined as a plant cell culture, plant cell line, plant tissue culture, lower plant, monocot plant cell culture, dicot plant cell culture, or progeny thereof derived from a transformed plant cell or protoplast, wherein the genome of the transformed plant contains foreign DNA, introduced by laboratory techniques, not originally present in a native, non-transgenic plant cell of the same species. The terms "transgenic plant" and "transformed plant" have sometimes been used in the art as synonymous terms to define a plant whose DNA contains an exogenous DNA molecule.

Construction of gene cassettes for transforming plants or transformed plant cell cultures can readily be accomplished by utilizing well known methods, such as those disclosed in Sambrook et al. (1989); and Ausubel et al., (1987) *Current Protocols in Molecular Biology*, John Wiley and Sons, New York, N.Y. The present invention also includes DNA sequences having substantial sequence homology with the disclosed sequences encoding immunoprotective antigens or proteinaceous agents such that they are able to have the disclosed effect on expression. As used in the present application, the term "substantial sequence homology" is used to indicate that a nucleotide sequence (in the case of DNA or RNA) or an amino acid sequence (in the case of a protein or polypeptide) exhibits substantial, functional or structural equivalence with another nucleotide or amino acid sequence. Any functional or structural differences between sequences having substantial sequence homology will be de minimis; that is they will not affect the ability of the sequence to function as indicated in the present application. Sequences that have substantial sequence homology with the sequences disclosed herein are usually variants of the disclosed sequence, such as mutations, but may also be synthetic sequences.

In most cases, sequences having 95% homology to the sequences specifically disclosed herein will function as equivalents, and in many cases considerably less homology, for example 75% or 80%, will be acceptable. Locating the parts of these sequences that are not critical may be time consuming, but is routine and well within the skill in the art. Exemplary techniques for modifying oligonucleotide sequences include using polynucleotide-mediated, site-directed mutagenesis. See Zoller et al. (1984); Higuchi et al. (1988); Ho et al. (1989); Horton et al. (1989); and *PCR Technology: Principles and Applications for DNA Amplification*, (ed.) Erlich (1989).

In preparing the constructs useful for this invention, the various DNA fragments may be manipulated, so as to provide for the DNA sequences in the proper orientation and, as appropriate, in the proper reading frame. Adapters or linkers may be employed for joining the DNA fragments or other manipulations may be involved to provide for convenient restriction sites, removal of superfluous DNA, removal of restriction sites, or the like.

In carrying out the various steps, cloning is employed, so as to amplify a vector containing the promoter/gene of interest for subsequent introduction into the desired host cells. A wide variety of cloning vectors are available, where the cloning vector includes a replication system functional in *E. coli* and a marker which allows for selection of the transformed cells. Illustrative vectors include pBR322, pUC series, pACYC184, Bluescript series (Stratagene) etc. Thus, the sequence may be inserted into the vector at an appropriate restriction site(s), the resulting plasmid used to transform the *E. coli* host (e.g., *E. coli* strains HB101, JMI101 and DH5α), the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

Vectors are available or can be readily prepared for transformation of plant cells. In general, plasmid or viral vectors should contain all the DNA control sequences necessary for both maintenance and expression of a heterologous DNA sequence in a given host. Such control sequences generally include a leader sequence and a DNA sequence coding for translation start-signal codon, a translation terminator codon, and a DNA sequence coding for a 3' UTR signal controlling messenger RNA processing. Selection of appropriate elements to optimize expression in any particular species is a matter of ordinary skill in the art utilizing the teachings of this disclosure. Finally, the vectors should desirably have a marker gene that is capable of providing a phenotypical property which allows for identification of host cells containing the vector.

The activity of the foreign coding sequence (e.g., immunoprotective agent or proteinaceous agent) inserted into plant cells is dependent upon the influence of endogenous plant DNA adjacent the insert. Generally, the insertion of heterologous genes appears to be random using any transformation technique; however, technology currently exists for producing plants with site specific recombination of DNA into plant cells (see WO 91/09957). Any method or combination of methods resulting in the expression of the desired sequence or sequences under the control of the promoter is acceptable.

The plant cell cultures provided herein are not limited to any particular method for transforming plant cells. Technology for introducing DNA into plant cells is well-known to those of skill in the art. Four basic methods for delivering foreign DNA into plant cells have been described. Chemical methods (Graham and van der Eb, *Virology,* 54(02):536-539, 1973; Zatloukal, Wagner, Cotten, Phillips, Plank, Steinlein, Curiel, Birnstiel, *Ann. N.Y. Acad. Sci.,* 660:136-153, 1992); Physical methods including microinjection (Capeechi, *Cell,* 22(2):479-488, 1980), electroporation (Wong and Neumann, *Biochem. Biophys. Res. Commun.* 107(2):584-587, 1982; Fromm, Taylor, Walbot, *Proc. Natl. Acad. Sci.* USA, 82(17): 5824-5828, 1985; U.S. Pat. No. 5,384,253) and the gene gun (Johnston and Tang, *Methods Cell. Biol.,* 43(A):353-365, 1994; Fynan, Webster, Fuller, Haynes, Santoro, Robinson, *Proc. Natl. Acad. Sci. USA* 90(24):11478-11482, 1993); Viral methods (Clapp, *Clin. Perinatol.,* 20(1):155-168, 1993; Lu, Xiao, Clapp, Li, Broxmeyer, *J. Exp. Med.* 178(6):2089-2096, 1993; Eglitis and Anderson, *Biotechniques,* 6(7):608-614, 1988; Eglitis, Kantoff, Kohn, Karson, Moen, Lothrop, Blaese, Anderson, *Avd. Exp. Med. Biol.,* 241:19-27, 1988); and Receptor-mediated methods (Curiel, Agarwal, Wagner, Cotten, *Proc. Natl. Acad. Sci. USA,* 88(19):8850-8854, 1991; Curiel, Wagner, Cotten, Birnstiel, Agarwal, Li, Loechel, Hu, *Hum. Gen. Ther.,* 3(2):147-154, 1992; Wagner et al., *Proc. Natl. Acad. Sci. USA,* 89 (13):6099-6103, 1992).

The introduction of DNA into plant cells by means of electroporation is well-known to those of skill in the art. Plant cell wall-degrading enzymes, such as pectin-degrading enzymes, are used to render the recipient cells more susceptible to transformation by electroporation than untreated cells. To effect transformation by electroporation one may employ either friable tissues such as a suspension culture of cells, or embryogenic callus, or immature embryos or other organized tissues directly. It is generally necessary to partially degrade the cell walls of the target plant material to pectin-degrading enzymes or mechanically wounding in a controlled manner. Such treated plant material is ready to receive foreign DNA by electroporation.

Another method for delivering foreign transforming DNA to plant cells is by microprojectile bombardment. In this method, microparticles are coated with foreign DNA and delivered into cells by a propelling force. Such micro particles are typically made of tungsten, gold, platinum, and similar metals. An advantage of microprojectile bombardment is that neither the isolation of protoplasts (Cristou et al., 1988, *Plant Physiol.,* 87:671-674) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen onto a filter surface covered with corn cells cultured in suspension. The screen disperses the particles so that they are not delivered to the recipient cells in large aggregates. For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

*Agrobacterium*-mediated transfer is a widely applicable system for introducing foreign DNA into plant cells because the DNA can be introduced into whole plant tissues, eliminating the need to regenerate an intact plant from a protoplast. The use of *Agrobacterium*-mediated plant integrating vectors to introduce DNA into plant cells is well known in the art. See, for example, the methods described in Fraley et al., 1985, *Biotechnology,* 3:629; Rogers et al., 1987, *Meth. in Enzymol.,* 153:253-277. Further, the integration of the Ti-DNA is a relatively precise process resulting in few rearrangements. The region of DNA to be transferred is defined by the border sequences, and intervening DNA is usually inserted into the plant genome as described in Spielmann et al., 1986, *Mol. Gen. Genet.,* 205:34; Jorgensen et al., 1987, *Mol. Gen. Genet.,* 207:471.

Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate construction of vectors capable of expressing various proteins or polypeptides. Convenient multi-linker regions flanked by a promoter and a polyadenylation site for direct expression of inserted polypeptide coding genes are suitable for present purposes. In addition, *Agrobacterium* containing both armed and disarmed Ti genes can be used for the transformations.

Transformation of plant protoplasts can be achieved using methods based on calcium phosphate precipitation, polyethylene glycol treatment, electroporation, and combinations of these treatments (see, e.g., Potrykus et al., 1985, *Mol. Gen. Genet.,* 199:183; Marcotte et al., *Nature,* 335:454, 1988). Application of these systems to different plant species depends on the ability to regenerate the particular species from protoplasts.

For practice of the present invention, it is preferable to transform plant cell lines that can be cultured and scaled-up rapidly. The use of plant cell cultures avoids open field production and greatly reduces the chances of gene escape and food contamination. Tobacco suspension cell cultures such NT-1 and BY-2 (Kato et al. 1972, Proc. IV IFS: Ferment. Technol. Today 689-695; An, G., 1985 *Plant Physiol.* 79, 568-570; Nagata et al. 1992, International Review of Cytology 132, 1-30) are preferred because these lines are particularly susceptible to handling in culture, are readily transformed, produce stably integrated events and are amenable to cryopreservation.

The tobacco suspension cell line, NT-1, is suitable for the practice of the present invention. NT-1 cells were originally developed from *Nicotiana tabacum* L. cv. bright yellow 2. The NT-1 cell line is widely used and readily available; though, any tobacco suspension cell line is consistent with the practice of the invention. Moreover, the cell line is variable and will change in response to culture conditions. NT-1 cells suitable for use in the examples below are available from the American Type Culture Collection under accession number ATCC No. 74840. See also U.S. Pat. No. 6,140,075, herein incorporated by reference in its entirety.

Many plant cell culture techniques and systems ranging from laboratory-scale shaker flasks to multi-thousand liter bioreactor vessels have been described and are well know in the art of plant cell culture. See, for example, Fischer, R. et al, 1999 *Biotechnol. Appl. Biochem.* 30, 109-112 and Doran, P., 2000 *Current Opinions in Biotechnology* 11, 199-204. After the transformed plant cells have been cultured to the mass desired, they are harvested, gently washed and placed in a suitable buffer for disruption. Many different buffers are compatible with the present invention. In general the buffer is an aqueous isotonic buffered salt solution at or near a neutral pH value that does not contain harsh detergents that can be used to solubilize membranes. Preferred buffers include Dulbecco's Phosphate Buffered Saline and PBS containing 1 mM EDTA.

After preparing a stably transformed plant cell line, the cultures of the present invention may be finished by confirming the gene insert (genetic event) using PCR amplification of the whole gene insert followed by restriction enzyme digestion. Master cell line and working cell lines should then be evaluated for bacterial and fungal contamination in accordance with procedure set forth in 9 CFR 113.26.

The initial recovery of master or working cells may be onto agar plates in the form of a callus. This may be followed by transfer to liquid suspension cultures. Passage ranges for working cell and production cultures may range from 1 to 50 or 100 times.

No ingredients of animal origin are used to grow the plant cell cultures of the present invention. Media for agar plates and suspension cultures are based on common plant culture media (Murashige and Skoog; MS) and are described in detail herein. Master cell lines are stored in the vapor phase of liquid nitrogen. Cultures maintained in this manner may be stored indefinitely and may be used to prepare callus cultures on agar medium. Working cell lines are stored in the vapor phase of liquid nitrogen and may be stored indefinitely and used to prepare callus cultures.

Master cell and working cell cultures used as inoculum for working cells or vaccine production may be maintained by periodic cycling of a callus on an agar plate or grown as a suspension culture. Frozen master cell or working cells may be thawed and passed to an agar plate and cultured one or more times at 25° C. for approximately one to two weeks. The callus is then teased apart and used to inoculate a flask of liquid suspension medium to produce a working cell or production culture. Working cell cultures used as inoculum for production cultures grown at room temperature with continuous agitation and passed in liquid suspension medium. Cultures are passed approximately every 3-14 days depending on the extent of growth observed and may be split 1:3 or 1:10 at each pass.

To produce a working cell line from a master cell agar plate, a healthy callus is selected, aseptically teased apart and portions placed into a flask containing liquid suspension medium. Working cell lines may also be passed from liquid culture to liquid culture using a 1:3 or 1:10 split while increasing the volume of the culture until a one liter volume is achieved in shaker flasks. One to three liters of shake flask culture may be transferred to a ten liter stirred tank as an inoculum. Production cultures are produced in a stirred tank with 100 liters working volume. A 100 liter fermenter may be inoculated at a 1:10 ratio of culture from a stirred tank or from multiple shaker flask cultures. Cultures in stirred tanks greater than ten liters are grown in liquid suspension medium without the selection agent.

The cultures are grown at ambient temperatures with continuous agitation for a period of 3-14 days for the working cell cultures. In most cases the working cell cultures are passed every 7 days with a 1:10 split. During scale-up of the working cells, the cultures are passed at a 1:10 split and are grown for at least seven days. The production cultures are grown for 7-15 days before harvest. Cultures are observed daily for characteristic growth, and samples of production cultures are aseptically removed periodically for microscopic examination and determination of packed cell volume. Cells should increase in density to a packed cell volume (PCV) of approximately 35% and should contain at least 50% healthy viable cells, based on a visual estimate, at the time of harvest. Microscopic examination of the cells should reveal a nucleus visible within the cells, but other cellular structures should not be observable.

Aeration may vary depending on the oxygen demand of the culture. Dissolved oxygen should be controlled between approximately 100% to 20%. Agitation speed may vary depending on the oxygen demand but should not to exceed 500 rpm. Controlling pH is typically not necessary. Production cultures may be harvested between 7 and 15 days post inoculation by gravity or vacuum filtration using conventional filtration media. Routine protein purification procedures many then be employed to isolate the pharmaceutical proteinaceous substance.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Vectors

Gene Construction: The coding sequence of the HN gene of NDV strain "Lasota" (Genbank accession AF077761), HA gene of AIV strain A Turkey/Wisconsin/68, VP2 gene of IBDV stain E19 (GenBank accession number X00493), and LT gene of *E. coli* were analyzed for codon use and the presence of undesired sequence motifs that could mediate spurious mRNA processing and instability, or methylation of genomic DNA. See Adang M J, Brody M S, Cardineau G, Eagan N, Roush R T, Shewmaker C K, Jones A, Oakes J V, McBride K E (1993) The construction and expression of *Bacillus thuringiensis* cryIIIA gene in protoplasts and potato plants. *Plant Mol Biol* 21:1131-1145. A plant-optimized coding sequence was designed with hybrid codon preference reflecting tomato and potato codon usage (Ausubel F., et al., eds. (1994) *Current Protocols in Molecular Biology*, vol. 3, p. A.1C.3 Haq T A, Mason H S, Clements J D, Arntzen C J (1995) Oral immunization with a recombinant bacterial antigen produced in transgenic plants. *Science* 268:714-716). The designed sequence for HN is shown in FIG. 1. The synthetic HN gene was assembled by a commercial supplier (Retrogen) and was received in two separate plasmids containing either the 5' (p4187-4203-1) or 3' (p42111-4235-1c-1) half of the gene cloned into pCR-Blunt.

Figure 3:
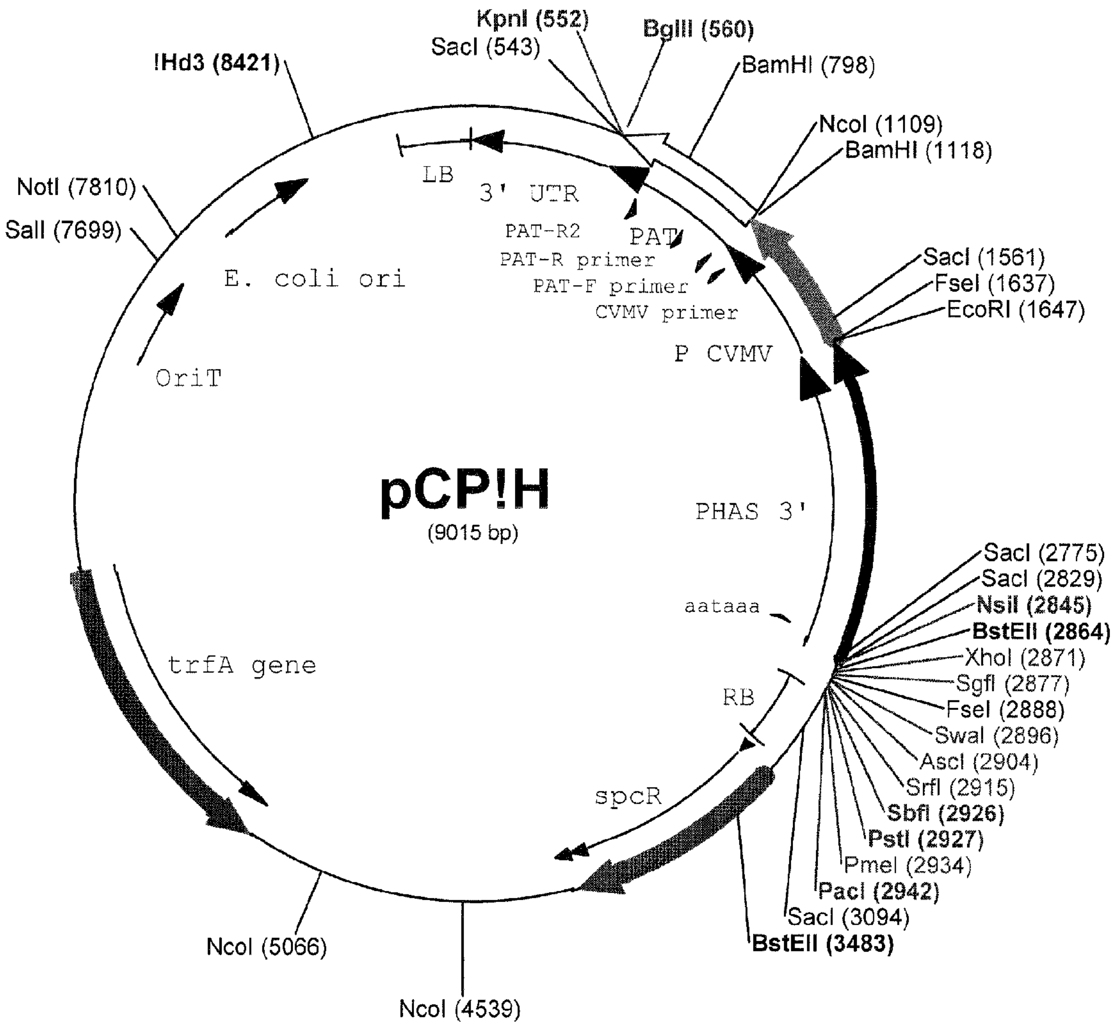
FIG. 3. Map of pCP!H which is a "template vector" used as a starting plasmid for a variety of plant expression vectors for expressing immunoprotective antigens.
Figure 4:
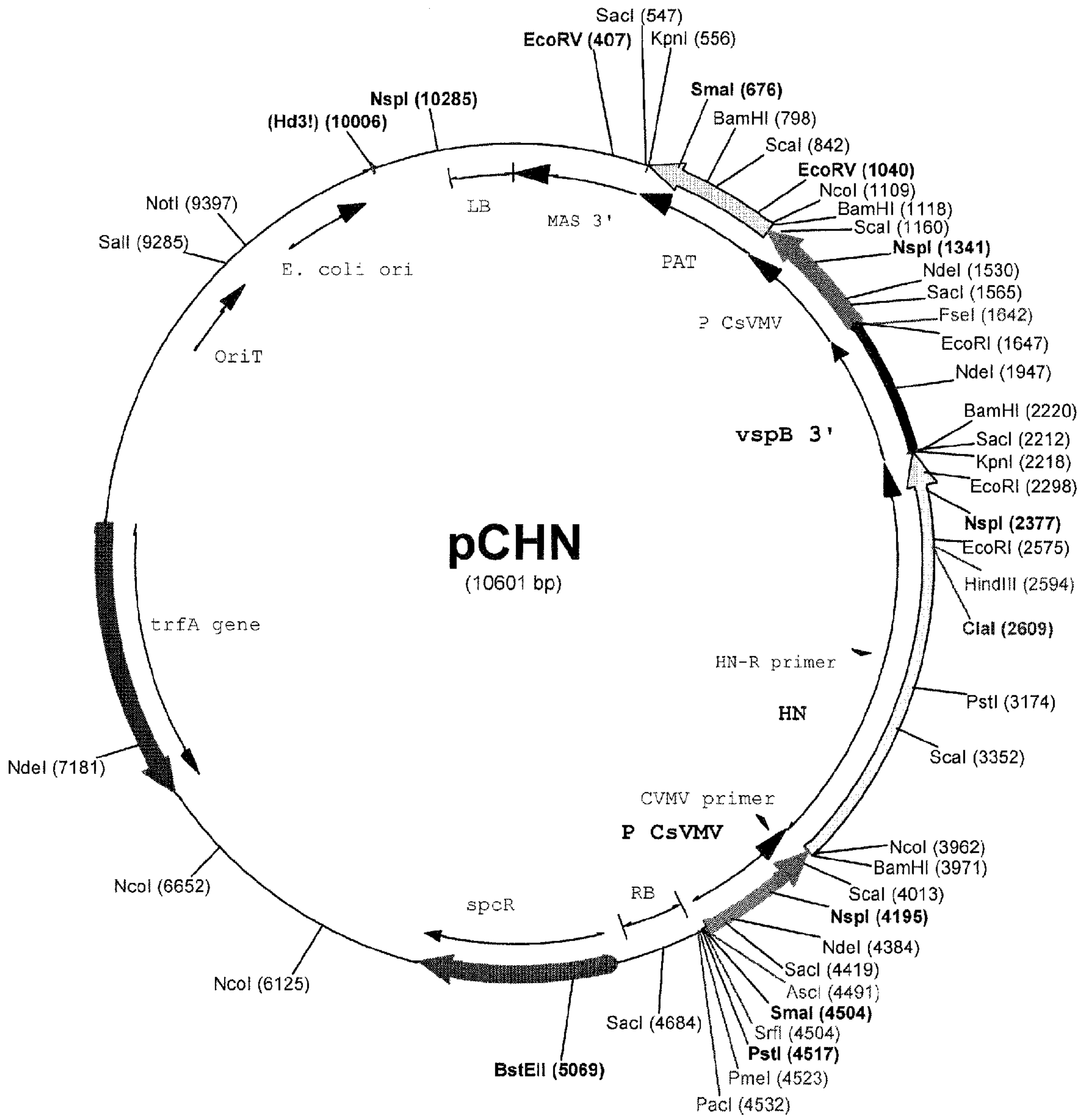
FIG. 4. Map of pCHN expression vector for NDV HN protein. The HN expression vector or cassette is driven by the constitutive CsVMV promoter and terminated by the soybean vspB 3' element.

Plasmid construction: Binary vectors for *Agrobacterium*-mediated plant transformations were constructed based on vector pBBV-PHAS-iaaH shown in FIG. 2, which uses the plant selection marker phosphinothricin acetyl transferase (PAT), described in U.S. Pat. Nos. 5,879,903; 5,637,489; 5,276,268; and 5,273,894 herein incorporated by reference, driven by the constitutive cassava vein mosaic virus promoter (CsVMV) described in WO 97/48819. We first deleted the iaaH gene and the phaseolin promoter sequence by digestion of pBBV-PHAS-iaaH with PacI and re-ligating to form pCVMV-PAT; then we deleted the single HindIII site by filling it with Klenow enzyme and re-ligating to form pCP!H. We end-tailored the CsVMV promoter by PCR using primers CVM-Asc (5'-ATGGCGCGCCAGAAGGTAATTATC-CAAG SEQ ID NO:5) and CVM-Xho (5'-ATCTCGAGC-CATGGTTTGGATCCA SEQ ID NO:6) on template pCP!H, and cloned the product in EcoRV-digested, T-tailed pBluescriptKS to make pKS-CVM7. A map of pCP!H is shown in FIG. 3. We constructed the HN expression cassette pKS-CHN by ligating the vector pKS-CVM7/NcoI-EcoRI with 3 insert fragments: the HN 5' half on NcoI/PstI, the HN 3' half on PstI/KpnI, and the soybean vspB 3' element on KpnI-EcoRI (Haq 1995). The binary T-DNA vector pCHN was then assembled by ligation of the vector pCP!H/AscI-EcoRI and the AscI-EcoRI fragment of pKS-CHN. A map of pCHN is shown in FIG. 4.

The granule bound starch synthase (GBSS) promoter, described in U.S. Pat. No. 5,824,798 herein incorporated by reference, was used to make other vectors. These constructs were made using a promoter fragment amplified from genomic DNA of *Solanum tuberosum* L. cv. "Desiree" using primers designed from the sequence in Genbank accession X83220 for the Chinese potato cultivar "Dongnong". A mutagenic primer "GSS-Nco" (5'-[TGCCATGGTGATGT-GTGGTCTACAA] SEQ ID NO:7) was used to create a Nco I site overlapping the translation initiation codon, along with forward primer "GSS-1.8F" (5'-[GATCTGACAAGTCAA-GAAAATTG] SEQ ID NO:8) complimentary to the 5' region at −1800 bp; the 1825 bp PCR product was cloned in T-tailed pBluescriptKS to make pKS-GBN, and sequenced. A mutagenic primer "GSS-Xho" (5'-[AGCTCGAGCTGTGT-GAGTGAGTG] SEQ ID NO:9) was used to create a XhoI site just 3' of the transcription start site along with primer "GSS-1.8F"; the 1550 bp PCR product was cloned in T-tailed pBluescriptKS to make pKS-GBX, and sequenced.

Figure 5:
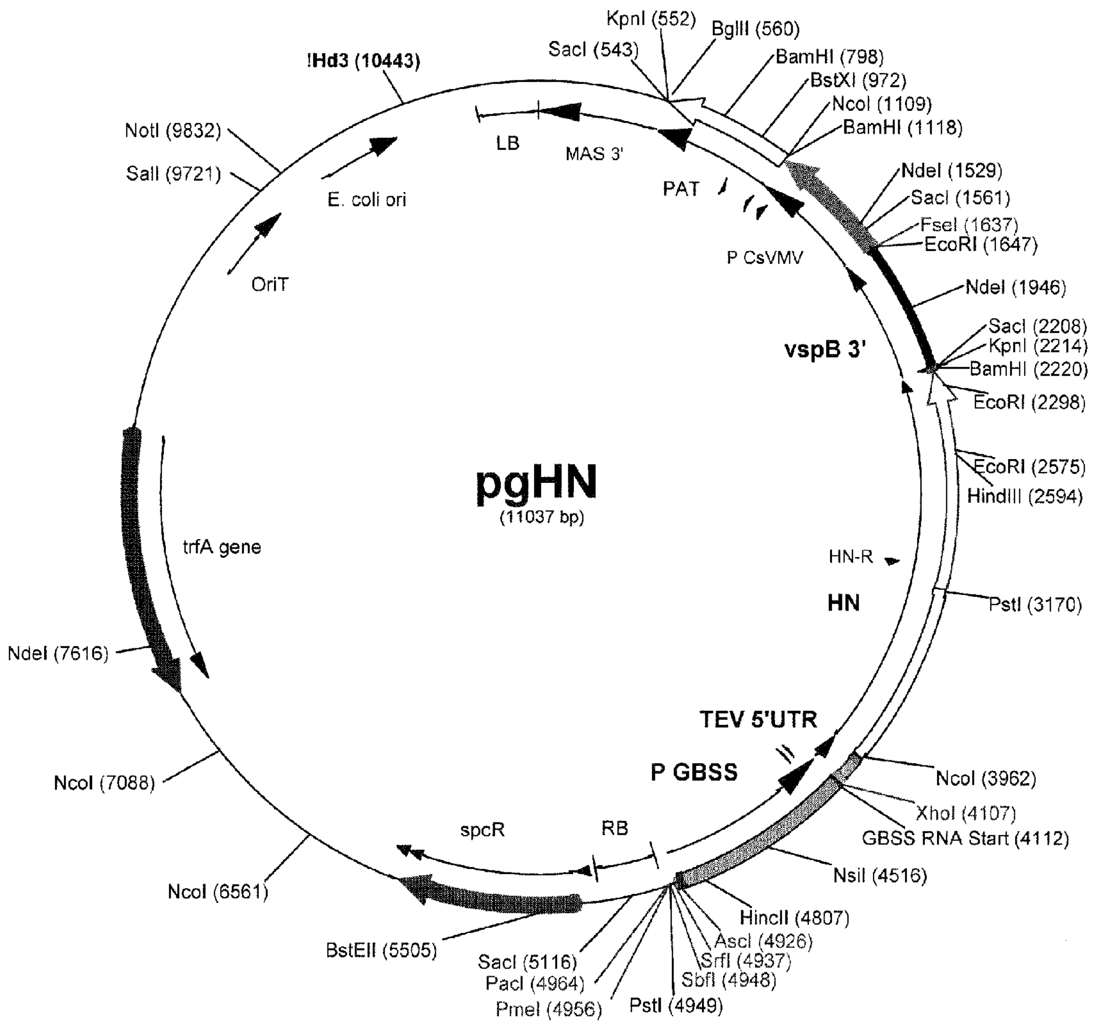
FIG. 5. Map of pgHN expression vector for NDV HN protein. The HN expression cassette is driven by the tuber-specific GBSS promoter with TEV 5' UTR and terminated by the soybean vspB 3' element.
Figure 11:
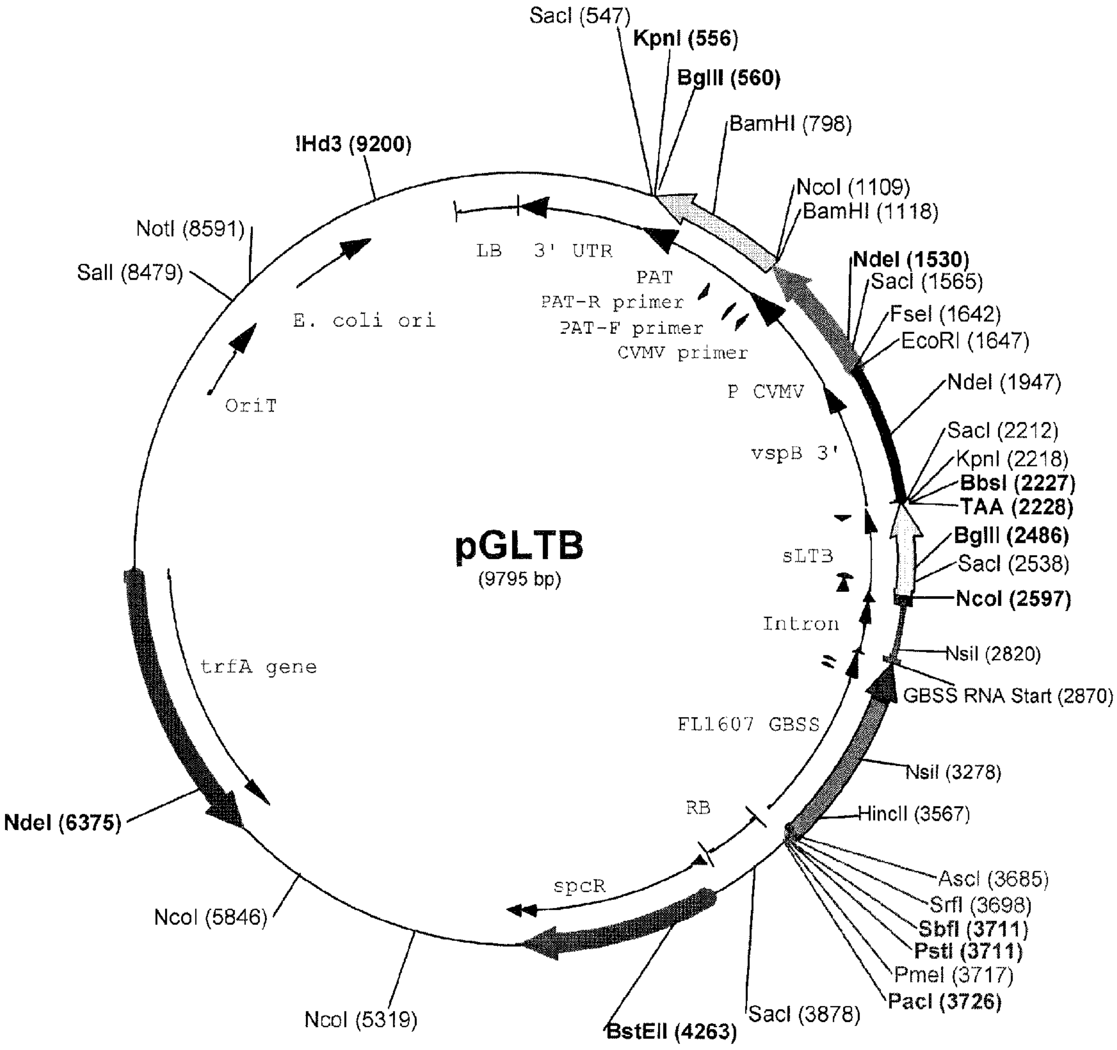
FIG. 11. Map of pGLTB intermediate vector.

A GBSS promoter expression cassette containing the TEV 5'UTR (untranslated region), described in U.S. Pat. No. 5,891,665 herein incorporated by reference, was assembled by ligation of vector pTH210 digested with HindIII/XhoI with the HindIII/XhoI fragment of pKS-GBX, which effected a substitution of the CaMV 35S promoter with the 811 bp GBSS promoter, to make pTH252A. See Haq T A, Mason H S, Clements J D, Arntzen C J (1995) Oral immunization with a recombinant bacterial antigen produced in transgenic plants. *Science* 268:714-716. The HN gene was inserted into pTH252A/NcoI-KpnI by ligation with the HN 5' half on NcoI/PstI and the HN 3' half on PstI/KpnI to make pHN252A. The binary T-DNA vector pgHN was made by ligation of the vector pGLTB (shown in FIG. 11) digested with NsiI and EcoRI with the fragments pHN252A/NsiI-KpnI and pTH210/KpnI-EcoRI. A map of pgHN is shown in FIG. 5.

Figure 6:
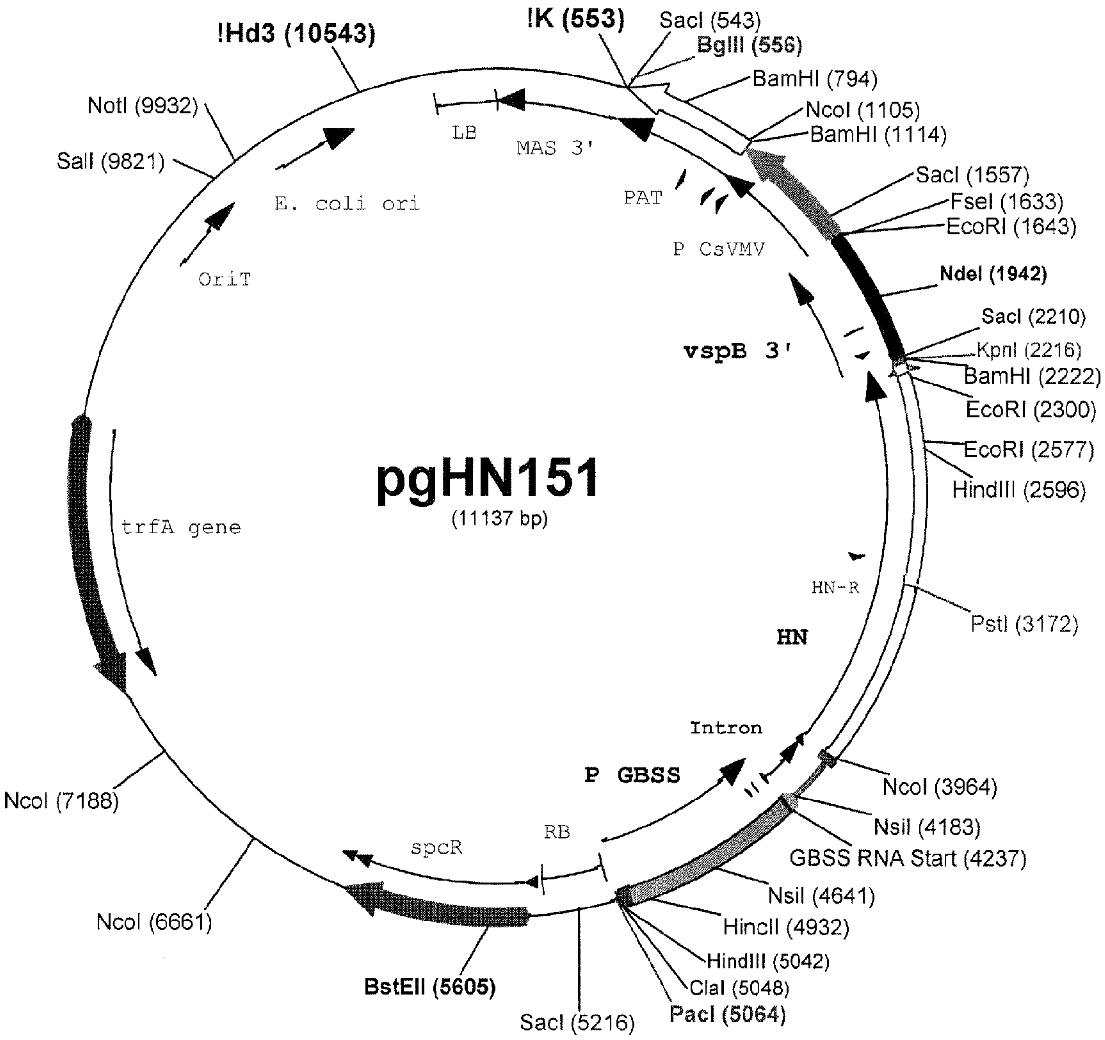
FIG. 6. Map of pgHN151 expression vector for NDV HN protein. The HN expression cassette is driven by the tuber-specific GBSS promoter with its native 5' UTR and intron, and terminated by the soybean vspB 3' element. The vector is derived from pBBV-PHAS-iaaH, containing the plant selectable marker PAT driven by the CsVMV promoter and terminated by the MAS 3' element. LB and RB, left and right T-DNA border elements that delineate the boundaries of the DNA that is integrated into the plant genome.

A GBSS promoter expression cassette containing the GBSS 5'UTR, described in U.S. Pat. No. 5,824,798, herein incorporated by reference, with its intron was assembled by ligation of vector pTH210 (Haq 1995) digested with HindIII/NcoI with the HindIII/NcoI fragment of pKS-GBN, which effected a substitution of the (cauliflower mosaic virus) CaMV 35S promoter/TEV 5'UTR with the 1084 bp GBSS promoter/5'-UTR, to make pTH251A. The binary T-DNA vector pgHN151 was made by ligation of the vector pCLT105 with fragments pTH251A/HindIII-NcoI and pHN252A/NcoI-KpnI. A map of pgHN151 is shown in FIG. 6.

Figure 7:
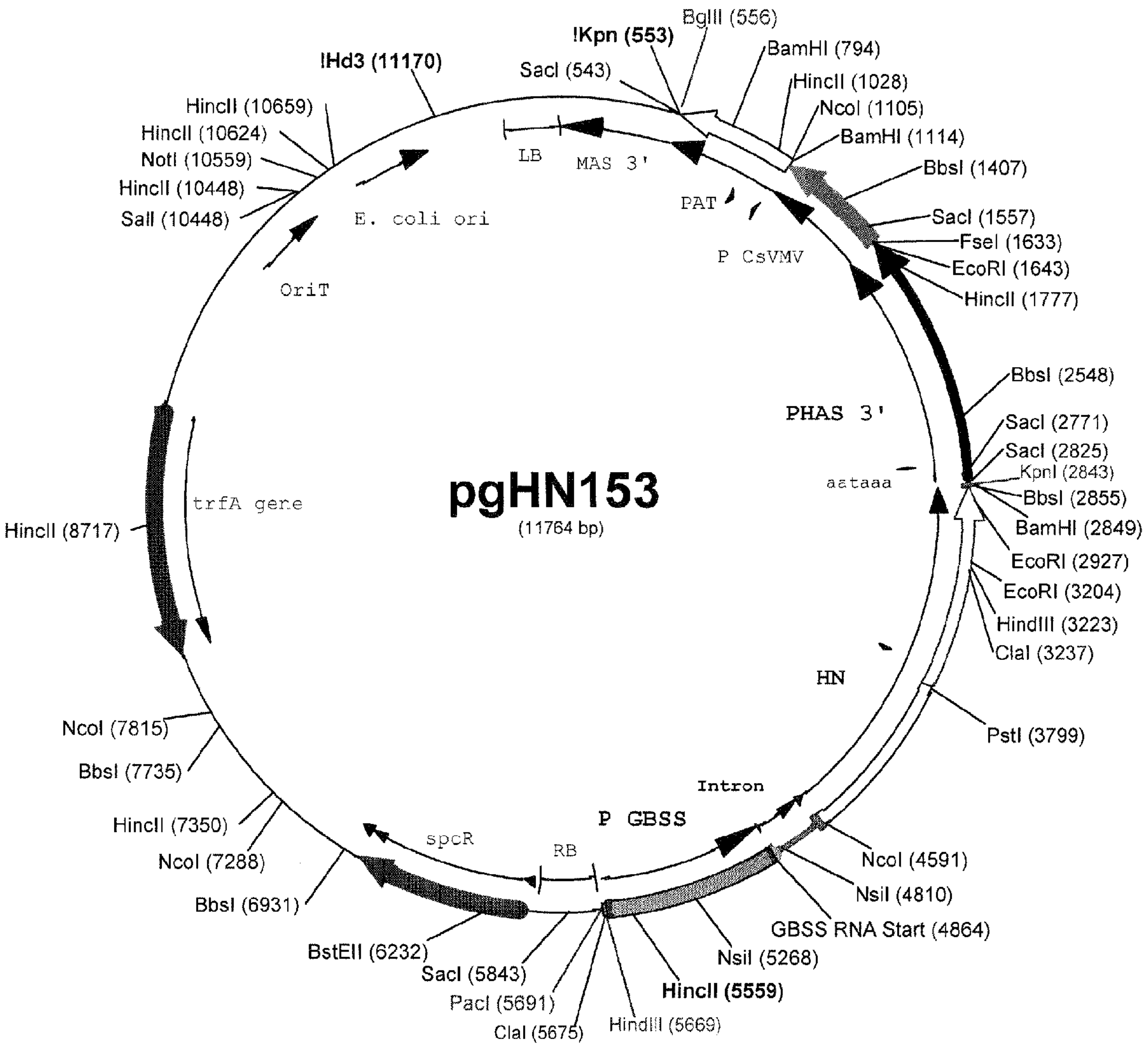
FIG. 7. Map of pgHN153 expression vector for NDV HN protein. The HN expression cassette is driven by the tuber-specific GBSS promoter with its native 5' UTR and intron, and terminated by the bean phaseolin 3' element. The vector is derived from pBBV-PHAS-iaaH, containing the plant selectable marker PAT driven by the CsVMV promoter and terminated by the MAS 3' element. LB and RB, left and right T-DNA border elements that delineate the boundaries of the DNA that is integrated into the plant genome.

A GBSS promoter expression cassette containing the GBSS 5'UTR with its intron and the bean phaseolin 3' element (described in U.S. Pat. Nos. 5,270,200; 6,184,437; 6,320,101, herein incorporated by reference) was constructed. First, pCP!H was digested at the unique KpnI site, blunted with T4 DNA polymerase, and re-ligated to make pCP!HK, which has the KpnI site removed. pCP!HK was digested with NsiI, followed by blunting with T4 DNA polymerase, and then digestion with PacI. The resulting vector was ligated with a 2848 bp fragment from pgHN151 digested with SacI, followed by blunting with T4 DNA polymerase, and then digestion with PacI, to make pgHN153. A map of pgHN153 is shown in FIG. 7.

Figure 8:
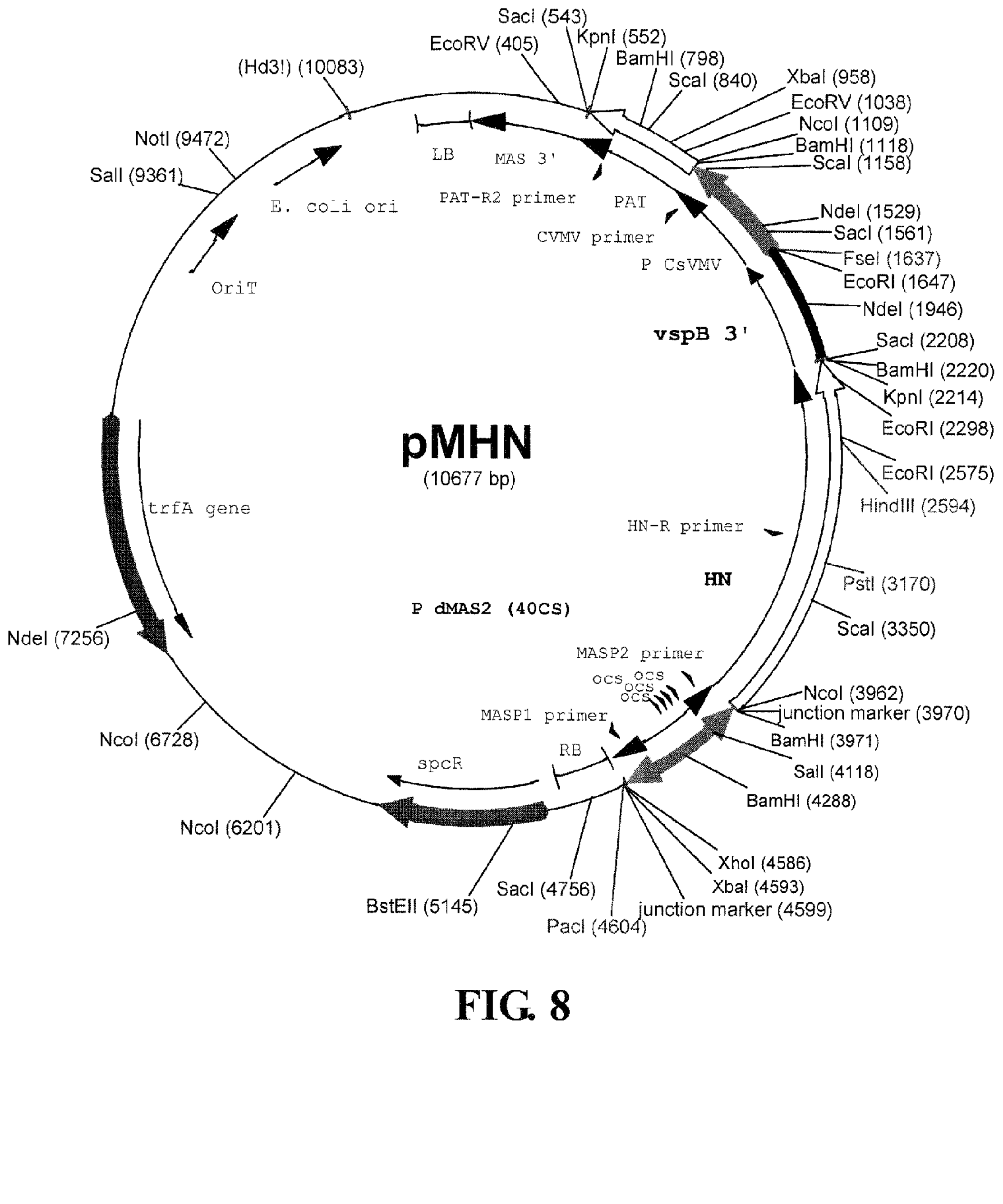
FIG. 8. Map of pMHN expression vector for NDV HN protein. The HN expression cassette is driven by the constitutive 4OCSΔMAS promoter (P2 direction) and terminated by the soybean vspB 3' element. The vector is derived from pBBV-PHAS-iaaH, containing the plant selectable marker PAT driven by the CsVMV promoter and terminated by the MAS 3' element. LB and RB, left and right T-DNA border elements that delineate the boundaries of the DNA that is integrated into the plant genome.

A chimeric constitutive promoter (4OCSΔMAS U.S. Pat. Nos. 5,001,060; 5,573,932 and 5,290,924 herein incorporated by reference) was used to construct another expression vector for HN. Plasmid, pAGM149, was digested with EcoRV and partial digestion with BamHI. This fragment was ligated with pCHN digested with PmeI/PstI and the 5' half of the synthetic HN gene obtained by digestion of pKS-CHN with BamHI/PstI. The resulting pMHN is shown in FIG. 8.

Figure 9:
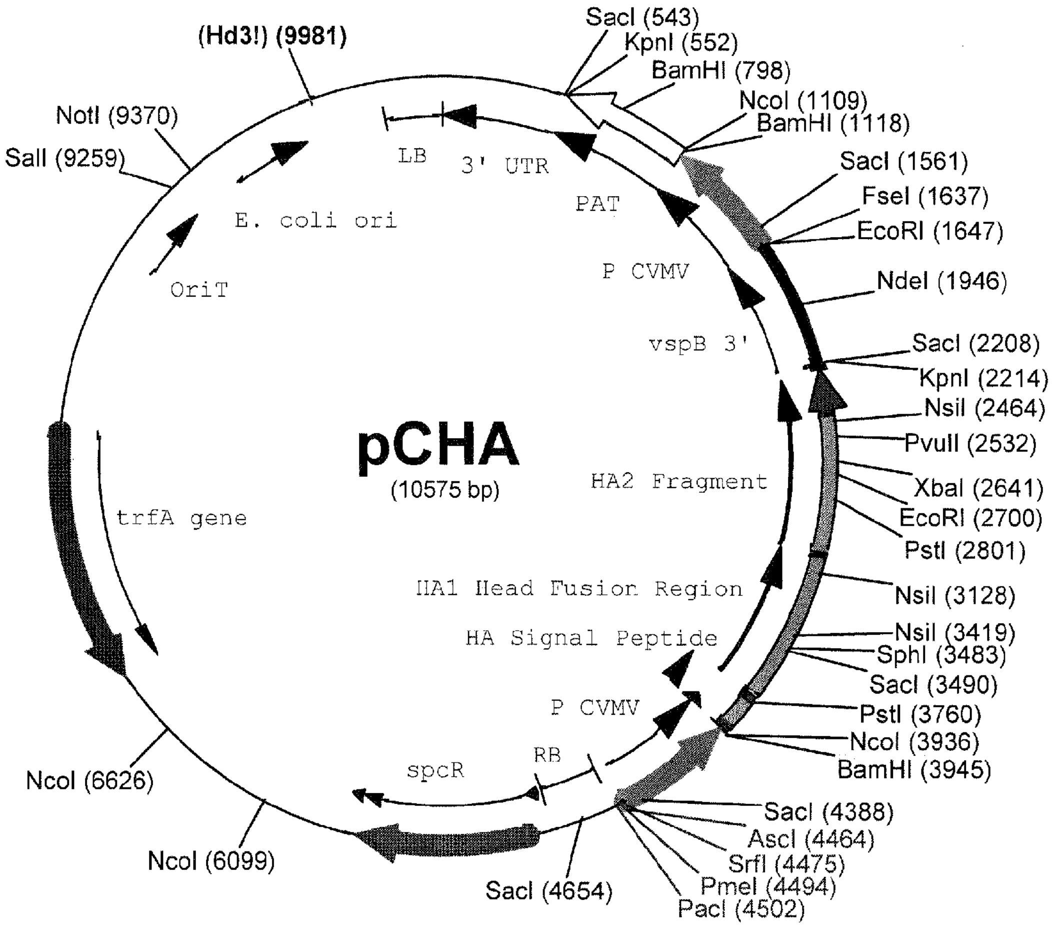
FIG. 9. Map of pCHA expression vector for the HA gene of the AIV A/turkey/Wisconsin/68 (H5N9).

A plasmid containing the HA gene of AIV A/turkey/Wisconsin/68 (H5N9) was obtained from David Suarez (SEPRL, Athens, Ga.) (FIG. 10). It was end-tailored by PCR to add restriction sites NcoI at 5' and KpnI at 3' end, and inserted into the vector pIB1210.1 (Haq et al., 1995), containing the 35S promoter, TEV 5'-UTR, and vspB 3' end. The expression cassette was transferred to the binary vector pGPTV-Kan (Becker et al., *Plant Mol Biol* 1992; 20: 1195-7) by digestion with HindIII and EcoRI (partial), to make pIBT-HAO. The HA gene/vspB3' end fragment from pIBT-HAO was obtained by digestion with NcoI and EcoRI (partial), and inserted into pKS-CVM7 to make pKS-CHA. The cassette containing the CsVMV promoter, HA gene, and vspB3' end was obtained from pKS-CHA by digestion with AscI and EcoRI (partial), and ligated with pCP!H to make pCHA, shown in FIG. 9.

Figure 12:
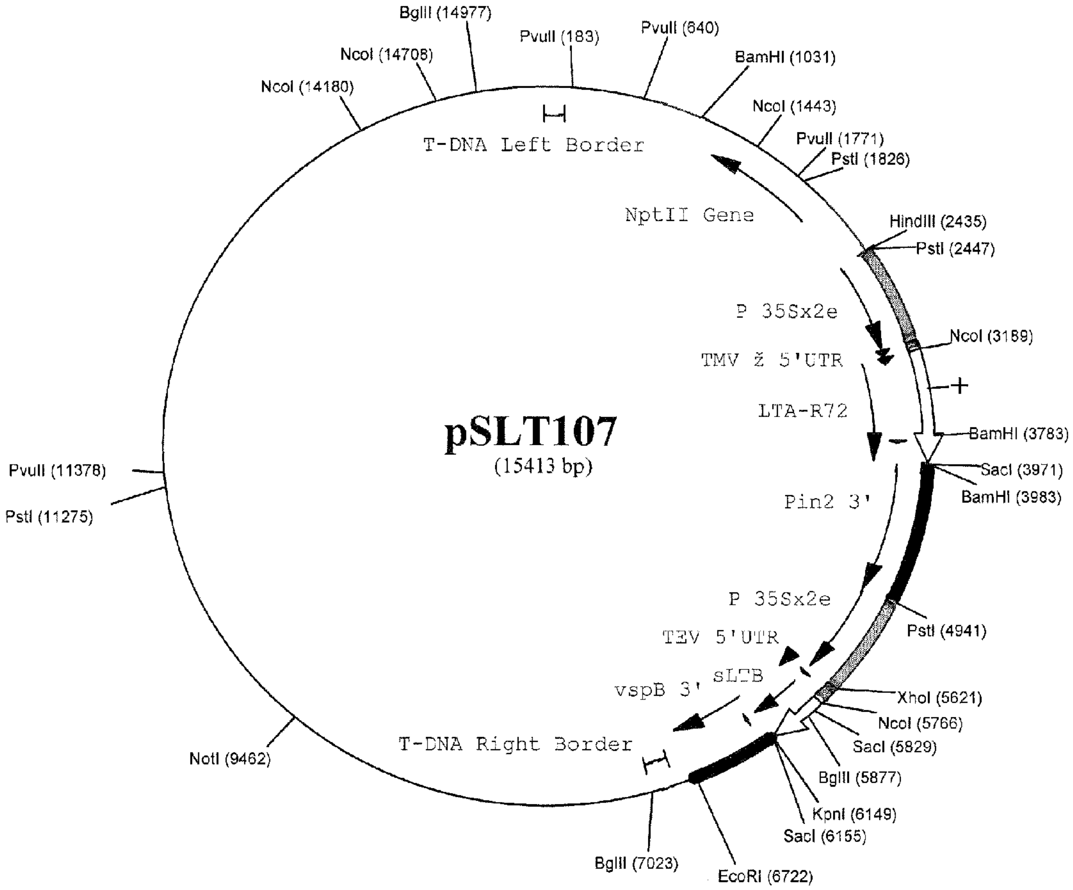
FIG. 12. Map of pSLT107 intermediate vector.

The plant-optimized sequence encoding the LT-B gene of *E. coli* strain H10407 is know in the art (Mason H S, Haq T A, Clements J D, Arntzen C J, 1998, *Vaccine* 16:1336-1343). The plant-optimized sequence encoding the LT-A gene of *E. coli* strain H10407 was described in WO/00/37609 which was originally filed as U.S. Provisional Application No. 60/113,507, the entire teachings of which are herein incorporated by reference. WO/00/37609 describes the construction of three binary T-DNA vectors (pSLT102, pSLT105, pSLT107) that were used for *Agrobacterium tumefaciens*-mediated plant cell transformation of *Nicotiana tabacium* NT-1 cells in Example 2. The resulting transformed NT-1 cell lines (SLT102, SLT105 and SLT107) expressed and accumulated fully assembled LT and LT analogs comprised of LT-B and modified forms of the LT-A subunit. FIG. 12 illustrates pSLT107, which contains a modified LT-A gene that replaces Ala72 with Arg72. SLT102 and SLT105 expression products were identical except that they contained different alterations in the LT-A gene (Ser63 to Lys63 in pSLT102; Arg192 to Gly192 in pSLT105. These lines contain an undetermined number of copies of the T-DNA region of the plasmids stably integrated into the nuclear chromosomal DNA. The transgenic NT1 cells accumulated LT-B subunits that assembled into ganglioside-binding pentamers, at levels up to 0.4% of total soluble protein as determined by ganglioside-dependent ELISA. The transgenic NT1 cells also accumulated modified LT-A subunits, some of which assembled with LT-B pentamers as determined by ganglioside-dependent ELISA using LT-A specific antibodies.

Figure 13:
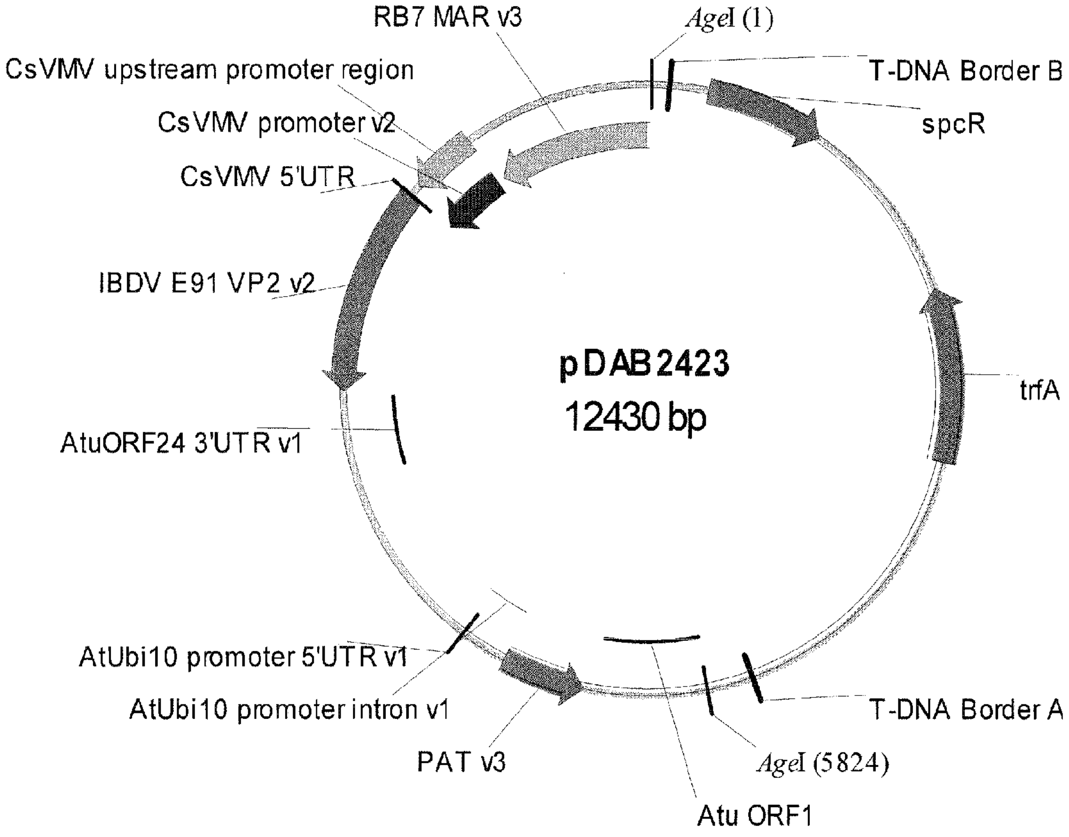
FIG. 13. pDAB2423. Binary vector encoding VP2.

A binary vector for *Agrobacterium*-mediated plant cell transformation was constructed from basic binary vector (pBBV) modified at the unique BamHI site with an AgeI linker for addition of a VP2 and selectable marker expression cassette. VP2 is flanked by an RB7 MAR element (U.S. Pat. No. 5,773,689; U.S. Pat. No. 5,773,695; U.S. Pat. No. 6,239, 328, WO 94/07902, and WO 97/27207) and the CsVMV promoter, with *Agrobacterium tumifaciens* (Atu) ORF 24 (GenBank accession number X00493) 3'UTR. The selectable marker, PAT, is regulated by *Arabidopsis thaliana* (At) Ubiquitin 10 promoter (Plant J. 1997. 11(5):1017; Plant Mol. Biol. 1993. 21(5):895; Genetics, 1995, 139(2):921) and Atu ORF 1 (U.S. Pat. No. 5,428,147; Plant Molecular Biology. 1983. 2:335; GenBank accession number X00493) 3' UTR; the resulting plasmid pDAB2423 is shown in FIG. 13.

Infectious Bursal Disease (IBD) virus, very virulent strain Ehime 91 (J Vet Med Sci. 1992. 54(1):153; JVI. 2002. 76(11): 5637) was used to produce the VP2 plant-optimized nucleotide sequence, based on reported VP2 amino acid sequence (GenBank accession number AB024076), with amino acids #454-456 from strain UK661 (GenBank accession number NC_004178). (See FIG. 14 for VP2 sequence).

Example 2

Preparation of Transgenic *Nicotiana Tabacum*

Three to 4 days prior to transformation, a 1 week old NT-1 culture was sub-cultured to fresh medium by adding 2 ml of the NT-1 culture into 40 ml NT-1 media. The sub-cultured was maintained in the dark at 25±1° C. on a shaker at 100 rpm.

NT-1 Medium

| Reagent | Per liter |
|---|---|
| MS salts | 4.3 g |
| MES stock (20X) | 50 ml |
| B1 inositol stock (100X) | 10 ml |
| Miller's I stock | 3 ml |
| 2,4-D (1 mg/ml) | 2.21 ml |
| Sucrose | 30 g |
| pH to 5.7 ± 0.03 | |

B1 Inositol Stock (100x)(1 liter)
Thiamine HCl (Vit B1) - 0.1 g
MES (20x) (1 liter)
MES (2-N-morpholinoethanesulfonic acid) - 10 g
Myoinositol - 10 g
Miller's I (1 liter)
$KH_2PO_4$ - 60 g

| MS Basal Salts | Per 1 liter DI water |
|---|---|
| Modified MS vitamins (100X) | 10 ml |
| Myo-inositol | 100 mg |
| Potassium Phosphate Dibasic Anhydrous | 137.4 g |
| MES | 0.5 g |
| 2,4-D (10 mg/ml) | 222 ul |
| Sucrose | 30 g |
| L-Proline | |

| Modified MS vitamins | Per Liter DI water |
|---|---|
| Nicotinic Acid | 5 mg/L |
| Pyridoxin HCL | 50 mg/L |
| Thiamine HCL | 200 mg/L |
| Glycine | 200 mg/L |

2.5M L-Proline Stock
M.W = 115.1 grams/L
Prepare 100 ml of 2.5M Stock
115.1/10 = 11.51 × 2.5 = 28.775 grams in 100 mls

*Agrobacterium tumefaciens* containing the expression vector of interest was streaked from a glycerol stock onto a plate of LB medium containing 50 mg/l spectinomycin. The bacterial culture was incubated in the dark at 30° C. for 24 to 48 hours. One well-formed colony was selected, and transferred to 3 ml of YM medium containing 50 mg/L spectinomycin. The liquid culture was incubated in the dark at 30° C. in an incubator shaker at 250 rpm until the $OD_{600}$ was 0.5-0.6. This took approximately 24 hrs.

| Reagent | Per liter |
|---|---|
| LB Medium | |
| Bacto-tryptone | 10 g |
| Yeast extract | 5 g |
| NaCl | 10 g |
| Difco Bacto Agar | 15 g |
| YM Medium | |
| Yeast extract | 400 mg |
| Mannitol | 10 g |
| NaCl | 100 mg |
| $MgSO_4 \cdot 7H_20$ | 200 mg |
| $KH_2PO_4$ | 500 mg |

(Alternatively, YM in powder form can be purchased (Gibco BRL; catalog #10090-011). To make liquid culture medium, add 11.1 g to 1 liter water.)

On the day of transformation, 1 µml of 20 mM acetosyringone was added per ml of NT-1 culture. The acetosyringone stock was made in ethanol the day of the transformation. The NT-1 cells were wounded to increase the transformation efficiency. For wounding, the suspension culture was drawn up and down repeatedly (20 times) through a 5 ml wide-bore sterile pipette. Four milliliters of the suspension was transferred into each of 10, 60×15 mm Petri plates. One plate was set aside to be used as a non-transformed control. Approximately, 50 to 100 µl of *Agrobacterium* suspension was added to each of the remaining 9 plates. The plates were wrapped with parafilm then incubated in the dark on a shaker at 100 rpm at 25±1° C. for 3 days.

Cells were transferred to a sterile, 50 ml conical centrifuge tube, and brought up to a final volume of 45 ml with NTC medium (NT-1 medium containing 500 mg/L carbenicillin, added after autoclaving). They were mixed, then centrifuged at 1000 rpm for 10 min in a centrifuge equipped with a swinging bucket rotor. The supernatant was removed, and the resultant pellet was resuspended in 45 ml of NTC. The wash was repeated. The suspension was centrifuged, the supernatant was discarded, and the pellet was resuspended in 40 ml NTC. Aliquots of 5 ml were plated onto each Petri plate (150×15 mm) containing NTCB 10 medium (NTC medium solidified with 8 g/l Agar/Agar; supplemented with 10 mg/l bialaphos, added after autoclaving). Plates were wrapped with parafilm then maintained in the dark at 25±1° C. Before transferring to the culture room, plates were left open in the laminar flow hood to allow excess liquid to evaporate. After 6 to 8 weeks, putative transformants appeared. They were selected and transferred to fresh NTCB5 (NTC medium solidified with 8 g/l Agar/Agar; supplemented with 5 mg/l bialaphos, added after autoclaving). The plates were wrapped with parafilm and cultured in the dark at 25±1° C.

Putative transformants appeared as small clusters of callus on a background of dead, non-transformed cells. These calli were transferred to NTCB5 medium and allowed to grow for several weeks. Portions of each putative transformant were selected for ELISA analysis. After at least 2 runs through ELISA, lines with the highest antigen levels were selected.

The amount of callus material for each of the elite lines was then multiplied in plate cultures and occasionally in liquid cultures.

Example 3

Stability of Plant Made Proteins

Proteins extracted from recombinant or native sources are often unstable due to proteases, glycosylases, lipases or other enzymes that co-purify with the protein and cellular components. The proteins and immunoprotective particles isolated from NT-1 cells are inherently stable and are robust to many different types of down stream processing activities. In FIG. 14, CHN-18 cells were harvested from a 10 liter fermentor in stationary phase and filtered, clarified by centrifugation and microfluidized. The supernatants were then filtered through a 0.2 or 0.45 micron filter to remove any bacterial agents that may have been introduced during manipulation through filtration or microfluidization, no stabilizers were added to these suspensions, the stability is inherent to the proteins derived from these transgenic cells. The material was then stored at 2-7° C., 25° C. or frozen at −80° C.; the material was found to be stable at all temperatures, but the most interesting results is that when held at 25° C. (ambient temperature) the isolated proteins were found to be stable (shown in FIG. 14). Although variation in signal was seen from month to month the amount of isolated protein showed remarkable stability after several months, the half life that can be calculated from these data indicate an extrapolated half life of 8 months (0.45 micron sample) and greater than one to several years for the 0.2 micron filtered sample.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Example 4

Media Formulations

The following are media formulations used for culturing native NT-1 cells and recombinant NT-1 cells on agar and in liquid suspensions. Additionally, the media formulation for cryopreserving NT-1 recombinant NT-1 is defined.

Media Preparation

A. Ingredients

Unless otherwise indicated, use reliable vendors for sourcing chemicals

| | |
|---|---|
| Agar | Potassium Iodide |
| Ammonium Nitrate | Potassium Nitrate |
| Boric Acid, Powder | Potassium Phosphate, Dibasic, $3^*H_2O$ |
| Calcium Chloride, Anhydrous | Potassium Phosphate, Dibasic, Anhydrous |
| Cobalt Chloride, $6^*H_2O$ | Potassium Phosphate, Monobasic |
| Copper (II) Sulfate, $5^*H_2O$ | L-Proline |
| Dimethyl sulfoxide (DMSO) | Pyroxidine HCl |
| EDTA, Disodium, $2^*H_2O$ | RO/DI water |

-continued

| | |
|---|---|
| Glycine | Sodium Chloride |
| Inositol | Sodium Molybdate, $2^*H_2O$ |
| Iron (II) Sulfate, $7^*H_2O$ | Sodium Phosphate, Dibasic, Anhydrous |
| Magnesium Sulfate, Anhydrous | Sucrose |
| Manganese Sulfate, $1^*H_2O$ | Thiamine HCl |
| MES, $1^*H_2O$ | Zinc Sulfate, $7^*H_2O$ |
| Murashige and Skoog salt mixture (MS salts) | Bialaphos, PhytoTechnology Labs, D-309 |
| Nicotinic Acid | 2,4-D, 10 mg/ml soln., PhytoTechnology Labs, B131 |
| Potassium Chloride | |

B. Formulations 1. 10× Batch Salts

| a. | Ingredients | Quantity/liter |
|---|---|---|
| | Ammonium Nitrate | 16.5 g |
| | Boric Acid, Powder | 62.0 mg |
| | Cobalt Chloride, $6^*H_2O$ | 0.25 mg |
| | Copper (II) Sulfate $5^*H_2O$ | 0.25 mg |
| | EDTA, Disodium, $2^*H_2O$ | 372.6 mg |
| | Iron (II) Sulfate $7^*H_2O$ | 278.0 mg |
| | Manganese Sulfate $1^*H_2O$ | 169.0 mg |
| | Sodium Molybdate, $2^*H_2O$ | 2.5 mg |
| | Potassium Iodide | 8.3 mg |
| | Potassium Nitrate | 19.0 g |
| | Potassium Phosphate, Monobasic | 1.7 g |
| | Zinc Sulfate, $7^*H_2O$ | 86.0 mg |
| | Magnesium Sulfate, Anhydrous | 1.807 g |
| | Calcium Chloride, Anhydrous | 3.322 g |
| | Thiamine HCl | 10.0 mg |
| | Inositol | 1.0 g |
| | MES, $1^*H_2O$ | 5.0 g |
| | RO/DI Water | 1000 mL |

b. Preparation i. Add 750 mL of RO/DI water to an appropriate container.

ii. Place the container on a heated stir plate and mix with a stir bar. It may be necessary to heat the water to dissolve all of the components.

iii. Add all of the ingredients to the water.

iv. After the final component is dissolved, bring the volume up to 1000 mL.

v. Sterilize the solution through a 0.2μ filter.

vi. Store at room temperature and assign a 1 year expiration date.

B. 2. Bialaphos (5 mg/mL)

| a. | Ingredients | Quantity/50 mL |
|---|---|---|
| | Bialaphos | 250.0 mg |
| | RO/DI water | 50 mL |

b. Preparation i. Add 50 mL of RO/DI water to an appropriate container.

ii. Place the container on a stir plate and mix with a stir bar.

iii. Add the Bialaphos to the water and mix until dissolved.

iv. Sterilize through a 0.2μ filter.

v. Store frozen and assign a 1 year expiration date.

B. 3. 100X Modified MS Vitamins

| a. | Ingredients | Quantity/liter |
|---|---|---|
| | Nicotinic Acid | 5.0 mg |
| | Pyroxidine HCl | 50.0 ml |
| | Thiamine HCl | 50.0 mg |
| | Glycine | 200.0 mg |
| | RO/DI Water | 1000 mL |

b. Preparation i. Add 500 mL of RO/DI water to an appropriate container.

ii. Place the container on a stir plate and mix with a stir bar.

iii. Add all of the components to the water.

iv. After the final component is dissolved, bring the volume to 1000 mL.

v. Sterilize through a 0.2µ filter.

vi. Store at 2° C.-10° C. and assign a 1 year expiration date.

B. 4. L-Proline (2.5 M)

| a. | Ingredients | Quantity/100 mL |
|---|---|---|
| | L-Proline | 28.775 g |
| | RO/DI Water | 100 mL |

b. Preparation i. Add 50 mL of RO/DI water to an appropriate container.

ii. Place the container on a stir plate and mix with a stir bar.

iii. Add the L-Proline to the water.

iv. After the L-Proline is dissolved, bring the volume up to 100 mL.

v. Store at 2° C.-10° C. and assign a 3 month expiration date.

B. 5. NT-1 Agar Plates

| a. | Ingredients | Quantity/liter |
|---|---|---|
| | Potassium Phosphate, Dibasic, $3{*}H_2O$ | 180.0 mg |
| | Sucrose | 30.0 g |
| | 10X batch salts | 100 mL |
| | 2,4-D (10 mg/ml) | 0.11 mL |
| | Agar | 8.0 g |
| | RO/DI water | 1000 mL |

b. Preparation i. Add 500 mL of RO/DI water to an appropriate container.

ii. Place the container on a heated stir plate and mix with a stir bar.

iii. Add all of the components to the water except the Agar.

iv. After the final component is dissolved, bring the volume up to 1000 mL.

v. Add the Agar to the solution and heat until the Agar is fully dissolved.

vi. While the solution is still hot, sterilize the solution through a 0.2µ filter.

vii. Allow the media to cool until it is close to room temperature.

viii. Pipette approximately 25 mL of agar into each 15 $cm^2$ sterile Petri dish and allow each plate to cool completely.

ix. Store plates inverted at 2° C.-10° C. and assign a 3 month expiration date.

B. 6. NT-1 Liquid Media

| a. | Ingredients | Quantity/liter |
|---|---|---|
| | Potassium Phosphate, Dibasic, $3{*}H_2O$ | 180.0 g |
| | Sucrose | 30.0 g |
| | 10X Batch Salts | 100 mL |
| | 2,4-D (10 mg/ml) | 0.11 mL |
| | RO/DI water | 1000 mL |

b. Preparation i. Add 500 mL of RO/DI water to an appropriate container.

ii. Place the container on a stir plate and mix with a stir bar.

iii. Add all of the components to the water.

iv. After the final component is dissolved, bring the volume to 1000 mL.

v. Dispense into 750 ml aliquots and autoclave at ≧121° C. for 30 minutes.

vi. Store at 2° C.-10° C. and assign a 1 year expiration date.

B. 7. NT1VP Media

| a. | Ingredients | Quantity/liter |
|---|---|---|
| | Murashige and Skoog Salt Mixture | 4.33 g |
| | 100X Modified MS Vitamins | 10.0 mL |
| | 2,4-D (10 mg/mL) | 222 uL |
| | L-Proline (2.5M) | 2.4 mL |
| | Potassium Phosphate, Dibasic, Anhydrous | 137.4 g |
| | MES | 500.0 mg |
| | Inositol | 100.0 mg |
| | Sucrose | 30.0 g |
| | RO/DI Water | 1000 mL |

b. Preparation i. Add 500 mL of RO/DI water to an appropriate container.

ii. Place the container on a stir plate and mix with a stir bar.

iii. Add all of the components to the water.

iv. After the final component is dissolved, bring the volume up to 1000 mL.

v. Dispense into 500 ml aliquots and autoclave at ≧121° C. for 30 minutes vi. Store at 2° C.-10° C. and assign a 1 year expiration date.

B. 8. Cryopreservation Media

| a. | Ingredients | Quantity |
|---|---|---|
| | NT1VP Media | 226.64 mL |
| | Glycerol | 46.06 g |
| | Sucrose | 342.27 g |
| | DMSO | 35.5 mL |

b. Preparation i. Add the glycerol to an appropriate container.

ii. Place the container on a heated stir plate and mix with a stir bar.

iii. Add the NT1VP Media to the container.

iv. Mix on low heat and slowly add the sucrose until dissolved.

v. Add the DMSO.

vi. Sterilize through a 0.2µ filter.

vii. Store the media at 2° C.-10° C. and assign a 1 year expiration date.

Example 5

Assessment of Plant Cell Growth Media and Suspension Cultures to Support Mycoplasma Growth The recombinant tobacco-derived plant cell line, CHN-18 NT-1, and the growth media disclosed herein do not support growth of mycoplasma. The objective of this study was to determine whether NT-1 growth media or suspension cultures of NT-1 and CHN-18 NT-1 can support the growth of two species of mycoplasma, *Mycoplasma hyorhinis* and *Acholeplasma laidlawii*.

The method followed 9 CFR 113.28. The test material was placed onto mycoplasma agar on day 0 of the test, before inoculation with mycoplasma, to demonstrate the absence of mycoplasma in the test material. The test material inoculated with the mycoplasma positive controls was not placed onto mycoplasma agar on day 0 of the test. The subcultures of the mycoplasma-inoculated test material to mycoplasma agar were performed on days 3, 7, 10 and 14. On the first day of the test, positive controls were prepared by inoculating mycoplasma broth and agar with mycoplasma positive controls. A negative control was prepared by inoculating mycoplasma broth and agar with mycoplasma broth. The positive and negative controls were subcultured onto mycoplasma agar on days 3, 7, 10 and 14. All of the mycoplasma agar plates were examined 10-14 days after inoculation for typical mycoplasma colonies.

The test materials were NT-1 plant cell growth media and CHN-18 plant cell growth media as well as the NT-1 and CHN-18 plant suspension cell cultures. The plant suspension cultures were inoculated with mycoplasma when they were actively growing, three to four day old cultures.

The NT-1 growth media did not support the growth of mycoplasma (Table 1). No mycoplasma colonies observed on any of the mycoplasma agar plates subcultured from NT-1 growth media inoculated with mycoplasma positive control organisms. The NT-1 media that was placed on agar plates before the mycoplasma positive controls were added also showed no mycoplasma growth. The positive controls had turbid growth in the mycoplasma broth and mycoplasma colonies were observed on all of the mycoplasma agar plates. The negative control had no growth in the myocplasma broth and there were no mycoplasma colonies on any of the mycoplasma agar plates.

TABLE 1

Mycoplasma growth in NT-1 growth media

| | Mycoplasma Colony Counts | | | | |
|---|---|---|---|---|---|
| | Day 0 | Day 3 | Day 7 | Day 10 | Day 14 |
| Negative Control | 0 | 0 | 0 | 0 | 0 |
| *M. hyorhinis* Positive Control | 33 | TNTC | TNTC | TNTC | TNTC |
| *A. laidlawii* Positive Control | TNTC | TNTC | TNTC | TNTC | TNTC |
| NT-1 Media + *M. hyorhinis* | ND | 0 | 0 | 0 | 0 |
| NT-1 Media + *A. laidlawii* | ND | 0 | 0 | 0 | 0 |

TNTC: too numerous to count, >100 colonies per plate
ND: not done,
NT-1 media without mycoplasma positive control organisms was tested on day 0 and had no mycoplasma colonies The NT-1 cell suspension culture did not support the growth of mycoplasma (Table 2). No mycoplasma colonies observed on any of the mycoplasma agar plates subcultured from a NT-1 cell suspension culture inoculated with mycoplasma positive control organisms. The NT-1 cell suspension culture that was placed on agar plates before the mycoplasma positive controls were added also showed no mycoplasma growth. The positive controls had turbid growth in the mycoplasma broth and mycoplasma colonies were observed on all of the mycoplasma agar plates. The negative control had no growth in the myocplasma broth and no mycoplasma colonies on any of the mycoplasma agar plates.

TABLE 2

Mycoplasma growth NT-1 suspension cell culture

| | Mycoplasma Colony Counts | | | | |
|---|---|---|---|---|---|
| | Day 0 | Day 3 | Day 7 | Day 10 | Day 14 |
| Negative Control | 0 | 0 | 0 | 0 | 0 |
| *M. hyorhinis* Positive Control | 33 | TNTC | TNTC | TNTC | TNTC |
| *A. laidlawii* Positive Control | TNTC | TNTC | TNTC | TNTC | TNTC |
| NT-1 Culture | 0 | ND | ND | ND | ND |
| NT-1 Culture + *M. hyorhinis* | ND | 0 | 0 | 0 | 0 |
| NT-1 Culture + *A. laidawii* | ND | 0 | 0 | 0 | 0 |

TNTC: too numerous to count, >100 colonies per plate
ND: not done,
NT-1 cell suspension culture without mycoplasma positive control organisms was tested on day 0 and had no mycoplasma colonies The CHN-18 growth media and cell suspension culture did not support the growth of mycoplasma (Table 3). There were no mycoplasma colonies observed on any of the mycoplasma agar plates subcultured from CHN-18 growth media or cell suspension culture that were inoculated with mycoplasma positive control organisms. No mycoplasma growth was observed on the CHN-18 media or CHN-18 cell suspension culture that was placed on agar plates before the mycoplasma positive controls were added. The positive controls had turbid growth in the mycoplasma broth and mycoplasma colonies were observed on all of the mycoplasma agar plates. The negative control had no growth in the myocplasma broth and no mycoplasma colonies on any of the mycoplasma agar plates.

TABLE 3

Mycoplasma growth in CHN-18 growth media and CHN-18 suspension cell culture

| | Mycoplasma Colony Counts | | | | |
|---|---|---|---|---|---|
| | Day 0 | Day 3 | Day 7 | Day 10 | Day 14 |
| Negative Control | 0 | 0 | 0 | 0 | 0 |
| *M. hyorhinis* Positive Control | 41 | TNTC | 53 | 41 | 13 |
| *A. laidlawii* Positive Control | TNTC | TNTC | TNTC | TNTC | TNTC |
| CHN-18 Media + *M. hyorhinis* | ND | 0 | 0 | 0 | 0 |
| CHN-18 Media + *A. laidlawii* | ND | 0 | 0 | 0 | 0 |
| CHN-18 Culture + *M. hyorhinis* | ND | 0 | 0 | 0 | 0 |
| CHN-18 Culture + *A. laidawii* | ND | 0 | 0 | 0 | 0 |

TNTC: too numerous to count, >100 colonies per plate
ND: not done,
CHN-18 growth media and cell suspension culture without mycoplasma positive control organisms were tested on day 0 and had no mycoplasma colonies Mycoplasma did not grow in either the NT-1 growth media used in production of the NT-1 cells or the CHN-18 growth media. Further, neither a suspension culture of NT-1 nor a suspension culture of CHN-18 cells was capable of supporting the growth of mycoplasma. These data demonstrate that the NT-1 and CHN-18 growth media, and cultures of NT-1 and CHN-18 cells are not capable of supporting the growth of mycoplasma.

We claim:

1. A plant cell culture for producing proteinaceous agents comprising:

a) an NT-1 cell stably transformed to express a transgene encoding a proteinaceous agent comprising SEQ ID NO:4 or SEQ ID NO:12; and b) a growth medium which supports the growth of said NT-1 cell in culture but which does not support the growth of Mycoplasmataceae and contains no materials of animal origin, said growth medium comprising no materials of animal origin and NT-1 liquid medium comprising:

| | Quantity/L |
|---|---|
| Potassium Phosphate, Dibasic, 3*$H_2O$ | 180.0 g |
| Sucrose | 30.0 g |
| 10X Batch Salts | 100 mL |
| 2,4-D (10 mg/ml) | 0.11 mL and |

RO/DI water added to bring the total volume to one liter, said 10X Batch Salt comprising the following compounds added to one liter of RO/DI water:

| | Quantity/L | |
|---|---|---|
| Ammonium Nitrate | 16.5 | g |
| Boric Acid, Powder | 62.0 | mg |
| Cobalt Chloride, 6*$H_2O$ | 0.25 | mg |
| Copper (II) Sulfate 5*$H_2O$ | 0.25 | mg |
| EDTA, Disodium, 2*$H_2O$ | 372.6 | mg |
| Iron (II) Sulfate 7*$H_2O$ | 278.0 | mg |
| Manganese Sulfate 1*$H_2O$ | 169.0 | mg |
| Sodium Molybdate, 2*$H_2O$ | 2.5 | mg |
| Potassium Iodide | 8.3 | mg |
| Potassium Nitrate | 19.0 | g |
| Potassium Phosphate, Monobasic | 1.7 | g |
| Zinc Sulfate, 7*$H_2O$ | 86.0 | mg |
| Magnesium Sulfate, Anhydrous | 1.807 | g |
| Calcium Chloride, Anhydrous | 3.322 | g |
| Thiamine HCl | 10.0 | mg |
| Inositol | 1.0 | g |
| MES, 1*$H_2O$ | 5.0 | g |

wherein said NT-1 cell is capable of being continuously passaged such that consistent transgene expression is maintained during passaging and wherein said NT-1 cell is capable of being cryopreserved such that consistent transgene expression is recovered upon recovery from cryopreservation.

2. The plant cell culture of claim 1, wherein said proteinaceous agent comprises SEQ ID NO: 4.

3. The plant cell culture of claim 1, wherein said proteinaceous agent comprises SEQ ID NO: 12.

4. A plant cell culture for producing proteinaceous vaccine antigen comprising:

a) a NT-1 cell stably transformed to express a transgene encoding a proteinaceous vaccine antigen comprising SEQ ID NO: 4 or SEQ ID NO:12; and b) a growth medium which supports the growth of said NT-1 cell in culture but which does not support the growth of Mycoplasmataceae and contains no materials of animal origin, said growth medium comprising no materials of animal origin and NT-1 liquid medium comprising:

| | Quantity/L |
|---|---|
| Potassium Phosphate, Dibasic, 3*$H_2O$ | 180.0 g |
| Sucrose | 30.0 g |
| 10X Batch Salts | 100 mL |
| 2,4-D (10 mg/ml) | 0.11 mL and |

RO/DI water added to bring the total volume to one liter, said 10X Batch Salt comprising the following compounds added to one liter of RO/DI water:

| | Quantity/L | |
|---|---|---|
| Ammonium Nitrate | 16.5 | g |
| Boric Acid, Powder | 62.0 | mg |
| Cobalt Chloride, 6*$H_2O$ | 0.25 | mg |
| Copper (II) Sulfate 5*$H_2O$ | 0.25 | mg |
| EDTA, Disodium, 2*$H_2O$ | 372.6 | mg |
| Iron (II) Sulfate 7*$H_2O$ | 278.0 | mg |
| Manganese Sulfate 1*$H_2O$ | 169.0 | mg |
| Sodium Molybdate, 2*$H_2O$ | 2.5 | mg |
| Potassium Iodide | 8.3 | mg |
| Potassium Nitrate | 19.0 | g |
| Potassium Phosphate, Monobasic | 1.7 | g |
| Zinc Sulfate, 7*$H_2O$ | 86.0 | mg |
| Magnesium Sulfate, Anhydrous | 1.807 | g |
| Calcium Chloride, Anhydrous | 3.322 | g |
| Thiamine HCl | 10.0 | mg |
| Inositol | 1.0 | g |
| MES, 1*$H_2O$ | 5.0 | g |

wherein said NT-1 cell is capable of being continuously passaged such that consistent transgene expression is maintained during passaging and wherein said NT-1 cell is capable of being cryopreserved such that consistent transgene expression is recovered upon recovery from cryopreservation.

5. The plant cell culture of claim 4, wherein said proteinaceous vaccine antigen comprises SEQ ID NO: 4.

6. The plant cell culture of claim 4, wherein said proteinaceous vaccine antigen comprises SEQ ID NO:12.

* * * * *

UNITED STATES PATENT AND TRADEMARK OFFICE

CERTIFICATE OF CORRECTION

PATENT NO. : 7,964,403 B2
APPLICATION NO. : 12/475864
DATED : June 21, 2011
INVENTOR(S) : Charles A. Mihaliak, Matthew J. Fanton and Janis K. McMillen It is certified that error appears in the above-identified patent and that said Letters Patent is hereby corrected as shown below:

Column 2,
Line 10, "of the cell;" should read --of the cell);--.
Line 21, "invention is provides" should read --invention provides--.

Column 3,
Line 34, "FIN gene" should read --HN gene--.

Column 4,
Line 35, "at a specified ranges" should read --at a specified range--.

Column 6,
Line 21, "such Dengue" should read --such as Dengue--.

Column 10,
Lines 47-48, "such NT-1" should read --such as NT-1--.

Column 12,
Line 16, "should not to exceed" should read --should not exceed--.

Column 14,
Line 45, "*tabacium*" should read --*tabacum*--.

Column 16,
Line 28, "1 μml" should read --1 μl--.

Signed and Sealed this
Eleventh Day of October, 2011

David J. Kappos
*Director of the United States Patent and Trademark Office*

SEQUENCE LISTING

```
<160> NUMBER OF SEQ ID NOS: 13

<210> SEQ ID NO 1
<211> LENGTH: 1753
<212> TYPE: DNA
<213> ORGANISM: Newcastle Disease Virus
<220> FEATURE:
<221> NAME/KEY: misc_feature
<222> LOCATION: (1)..(1753)
<223> OTHER INFORMATION: See Figures 1a and 1b.
<220> FEATURE:
<221> NAME/KEY: misc_feature
<222> LOCATION: (1)..(1753)
<223> OTHER INFORMATION: Plant optimized coding sequence of the
      hemaglutinin/neuraminidase (HN) gene of Newcastle Disease Virus
      (NDV) strain "Lasota"

<400> SEQUENCE: 1

atggacagag cagtttcaca agtggcccta gagaatgatg agagggaagc caagaatacc     60

tggaggctta tattcagaat agccatctta ttccttactg tggtcaccct agcaatctct    120

gttgcatccc tcctctattc tatgggagca agcacccccct cagacttggt gggcataccc    180

acaagaatct ctagggcaga agaaaaaatc accagtaccc ttggctccaa ccaagatgtt    240

gtggacagaa tctacaaaca ggtggcactt gaaagtccac ttgcattact caacacagag    300

actaccatca tgaatgcaat taccagccta tcctatcaaa ttaatggggc tgccaacaat    360

tcaggttggg gagccccaat tcatgatcca gactatattg gaggtattgg caaagagctt    420

attgtagatg atgcttcaga tgttacatct ttctatcctt cagctttcca ggaacacctg    480

aatttcattc ctgcacccac aactgggagt gggtgcacta gaatacccctc atttgacatg    540

agtgctacac actactgcta cacacataat gttattctct ctggctgtag ggaccactct    600

cactcttatc aatacttagc tcttggagtt ctcagaacat ctgctactgg tagagtcttt    660

ttctcaactc ttaggagtat caacctagat gatacacaaa ataggaaaag ttgctctgta    720

tctgctacac ctttgggctg tgatatgcta tgcagtaaag taacagaaac tgaagaagag    780

gactataatt ctgctgtccc tacaaggatg gtgcatggca gattgggttt tgatggtcaa    840

tatcatgaaa aagatttgga tgtcactaca ttgtttgggg attgggtagc taattaccca    900

ggagttggag gtggtagctt cattgactcc agagtctggt tctctgtcta tggtggttta    960

aaacctaaca gtcctagtga tactgtgcaa gagggaaagt atgttatcta caagaggtat   1020

aatgatactt gtcctgatga acaggattac cagattagga tggctaagtc atcatacaaa   1080

ccaggaagat ttggaggtaa gaggatacaa caagctattt tgagtattaa ggttagcaca   1140

tcattgggag aggacccagt ccttactgtt ccaccaaaca ctgtaacact catgggagct   1200

gagggaagga ttttaactgt tggtactagc cattttcttt atcagagagg aagttcctat   1260

tttagcccag cattactgta tccaatgact gtgagcaaca agacagctac attacattca   1320

ccatatactt ttaatgcttt tacaagacct ggatcaattc cttgccaggc ttcagctaga   1380

tgtccaaatt catgtgtgac tggagtttac actgatcctt accctttgat attttacaga   1440

aatcatacct tgagaggggt ttttggaaca atgttggatg gtgttcaagc taggctcaat   1500

cctgcctctg ctgtttttga ttctacatca agatcaagaa taaccagggt ttcctctagt   1560
```

-continued

```
tccactaagg cagcatatac tacctccaca tgtttcaaag ttgtaaagac taacaaaact   1620

tattgtctga gcatagctga gatctctaac actctttttg gggagttcag aattgttcca   1680

cttttggtgg aaattctgaa ggatgatggt gtaagggaag caagatctgg ttaagtcttc   1740

aggtaccgag ctc                                                      1753
```

<210> SEQ ID NO 2
<211> LENGTH: 577
<212> TYPE: PRT
<213> ORGANISM: Newcastle Disease Virus
<220> FEATURE:
<221> NAME/KEY: misc_feature
<223> OTHER INFORMATION: See Figures 1a and 1b.
<220> FEATURE:
<221> NAME/KEY: misc_feature
<223> OTHER INFORMATION: Plant optimized protein sequence of the hemaglutinin/neuraminidase (HN) gene of Newcastle Disease Virus (NDV) strain "Lasota"

<400> SEQUENCE: 2

```
Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Phe Leu
            20                  25                  30

Thr Val Val Thr Leu Ala Ile Ser Val Ala Ser Leu Leu Tyr Ser Met
        35                  40                  45

Gly Ala Ser Thr Pro Ser Asp Leu Val Gly Ile Pro Thr Arg Ile Ser
    50                  55                  60

Arg Ala Glu Glu Lys Ile Thr Ser Thr Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
            180                 185                 190

Leu Ser Gly Cys Arg Asp His Ser His Ser Tyr Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
                245                 250                 255

Thr Glu Glu Glu Asp Tyr Asn Ser Ala Val Pro Thr Arg Met Val His
            260                 265                 270

Gly Arg Leu Gly Phe Asp Gly Gln Tyr His Glu Lys Asp Leu Asp Val
        275                 280                 285

Thr Thr Leu Phe Gly Asp Trp Val Ala Asn Tyr Pro Gly Val Gly Gly
    290                 295                 300
```

-continued

```
Gly Ser Phe Ile Asp Ser Arg Val Trp Phe Ser Val Tyr Gly Gly Leu
305                 310                 315                 320

Lys Pro Asn Ser Pro Ser Asp Thr Val Gln Glu Gly Lys Tyr Val Ile
                325                 330                 335

Tyr Lys Arg Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
        355                 360                 365

Ile Gln Gln Ala Ile Leu Ser Ile Lys Val Ser Thr Ser Leu Gly Glu
    370                 375                 380

Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Ser
            420                 425                 430

Asn Lys Thr Ala Thr Leu His Ser Pro Tyr Thr Phe Asn Ala Phe Thr
        435                 440                 445

Arg Pro Gly Ser Ile Pro Cys Gln Ala Ser Ala Arg Cys Pro Asn Ser
    450                 455                 460

Cys Val Thr Gly Val Tyr Thr Asp Pro Tyr Pro Leu Ile Phe Tyr Arg
465                 470                 475                 480

Asn His Thr Leu Arg Gly Val Phe Gly Thr Met Leu Asp Gly Val Gln
                485                 490                 495

Ala Arg Leu Asn Pro Ala Ser Ala Val Phe Asp Ser Thr Ser Arg Ser
            500                 505                 510

Arg Ile Thr Arg Val Ser Ser Ser Ser Thr Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Gly


<210> SEQ ID NO 3
<211> LENGTH: 1647
<212> TYPE: DNA
<213> ORGANISM: Avian Influenze Virus
<220> FEATURE:
<221> NAME/KEY: misc_feature
<222> LOCATION: (1)..(1647)
<223> OTHER INFORMATION: See Figure 10
<220> FEATURE:
<221> NAME/KEY: misc_feature
<222> LOCATION: (1)..(1647)
<223> OTHER INFORMATION: DNA sequence of the hemagglutinin (HA) gene of
      Avian Influenza Virus (AIV) A/turkey/Wisconsin/68 (H5N9).

<400> SEQUENCE: 3

gaccaaatct gcatcggtta tcatgcaaac aattcaacaa aacaagttga cacaatcatg     60

gagaagaatg tgacggtcac acatgctcaa gatatactgg aaaaagagca caacgggaaa    120

ctctgcagtc tcaaaggagt gaggcccctc attctgaagg attgcagtgt ggctggatgg    180

cttcttggga acccaatgtg tgatgagttc ctaaatgtac cggaatggtc atatattgta    240

gagaaggaca atccaaccaa tggcttatgt tatccgggag acttcaatga ttatgaagaa    300
```

-continued

```
ctgaagtatt taatgagcaa cacaaaccat tttgagaaaa ttcaaataat ccctaggaac    360

tcttggtcca atcatgatgc ctcatcagga gtgagctcag catgcccata caatggtagg    420

tcttcctttt tcaggagtgt ggtgtggttg atcaagaaga gtaatgtata cccaacaata    480

aagaggacct acaataacac caatgtagag gaccttctga tattgtgggg aatccatcac    540

cctaatgatg cagcggaaca aacggaactc tatcagaact cgaacactta tgtgtctgta    600

ggaacatcaa cactaaatca gaggtcaatt ccagaaatag ctaccaggcc caaagtgaat    660

ggacaaagtg gaagaataga atttttctgg acaatactaa ggccgaacga tgcaatcagc    720

tttgaaagta atgggaactt tatagctcct gaatatgcat acaagatagt taaaaaggga    780

gattcagcaa tcatgagaag cgaactggag tatggcaact gtgataccaa atgtcagacc    840

ccagtgggtg ctataaattc cagtatgcct tttcacaatg ttcatcccct taccattgga    900

gagtgtccca aatatgtcaa atcagataaa ctggtccttg caacaggact gaggaacgtg    960

cctcagagag aaacaagagg tctgtttgga gcaatagcag gattcataga aggggggtgg   1020

caaggaatgg tagatggatg gtatggttac catcatagca acgagcaggg aagtggatat   1080

gctgcagaca aagagtccac tcagaaagca atcgacggga tcaccaataa agtcaactca   1140

atcattgaca aaatgaacac tcaattcgaa gccgttggga aagaattcaa caacttagaa   1200

aggagaatag aaaatttgaa taagaaaatg gaagatggat ttctagatgt atggacttac   1260

aatgcagaac ttctggtgct catggaaaat gaaagaactc tggatttcca tgattcatat   1320

gtcaagaacc tatacgataa ggtccgactc cagctgagag ataatgcaaa agaattgggc   1380

aatgggtgtt tggagttctc ccacaaatgt gacaatgaat gcatggaaag tgtgagaaac   1440

ggaacgtatg actatccaca atactcagaa gaatcaaggc tgaacagaga ggaaatagat   1500

ggagtcaaat tggagtcaat gggcacctat cagatactat caatttactc aacagtggcg   1560

agttccctag cactggcaat catggtagct ggtctgtctt tttggatgtg ctccaatgga   1620

tcattgcaat gcagaatttg catctag                                        1647
```

```
<210> SEQ ID NO 4
<211> LENGTH: 548
<212> TYPE: PRT
<213> ORGANISM: Avian Influenze Virus
<220> FEATURE:
<221> NAME/KEY: misc_feature
<223> OTHER INFORMATION: See Figure 10.
<220> FEATURE:
<221> NAME/KEY: misc_feature
<223> OTHER INFORMATION: Protein sequence of the hemagglutinin (HA) gene
      of Avian Influenza Virus (AIV) A/turkey/Wisconsin/68 (H5N9).

<400> SEQUENCE: 4

Asp Gln Ile Cys Ile Gly Tyr His Ala Asn Asn Ser Thr Lys Gln Val
1               5                   10                  15

Asp Thr Ile Met Glu Lys Asn Val Thr Val Thr His Ala Gln Asp Ile
            20                  25                  30

Leu Glu Lys Glu His Asn Gly Lys Leu Cys Ser Leu Lys Gly Val Arg
        35                  40                  45

Pro Leu Ile Leu Lys Asp Cys Ser Val Ala Gly Trp Leu Leu Gly Asn
    50                  55                  60

Pro Met Cys Asp Glu Phe Leu Asn Val Pro Glu Trp Ser Tyr Ile Val
65                  70                  75                  80

Glu Lys Asp Asn Pro Thr Asn Gly Leu Cys Tyr Pro Gly Asp Phe Asn
                85                  90                  95
```

-continued

```
Asp Tyr Glu Glu Leu Lys Tyr Leu Met Ser Asn Thr Asn His Phe Glu
            100                 105                 110

Lys Ile Gln Ile Ile Pro Arg Asn Ser Trp Ser Asn His Asp Ala Ser
        115                 120                 125

Ser Gly Val Ser Ser Ala Cys Pro Tyr Asn Gly Arg Ser Ser Phe Phe
    130                 135                 140

Arg Ser Val Val Trp Leu Ile Lys Lys Ser Asn Val Tyr Pro Thr Ile
145                 150                 155                 160

Lys Arg Thr Tyr Asn Asn Thr Asn Val Glu Asp Leu Leu Ile Leu Trp
                165                 170                 175

Gly Ile His His Pro Asn Asp Ala Ala Glu Gln Thr Glu Leu Tyr Gln
            180                 185                 190

Asn Ser Asn Thr Tyr Val Ser Val Gly Thr Ser Thr Leu Asn Gln Arg
        195                 200                 205

Ser Ile Pro Glu Ile Ala Thr Arg Pro Lys Val Asn Gly Gln Ser Gly
    210                 215                 220

Arg Ile Glu Phe Phe Trp Thr Ile Leu Arg Pro Asn Asp Ala Ile Ser
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Arg Ser Glu Leu Glu Tyr Gly
            260                 265                 270

Asn Cys Asp Thr Lys Cys Gln Thr Pro Val Gly Ala Ile Asn Ser Ser
        275                 280                 285

Met Pro Phe His Asn Val His Pro Leu Thr Ile Gly Glu Cys Pro Lys
    290                 295                 300

Tyr Val Lys Ser Asp Lys Leu Val Leu Ala Thr Gly Leu Arg Asn Val
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Ile Thr Asn Lys Val Asn Ser Ile Ile Asp Lys
    370                 375                 380

Met Asn Thr Gln Phe Glu Ala Val Gly Lys Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Tyr Val Lys Asn Leu Tyr Asp Lys Val
        435                 440                 445

Arg Leu Gln Leu Arg Asp Asn Ala Lys Glu Leu Gly Asn Gly Cys Leu
    450                 455                 460

Glu Phe Ser His Lys Cys Asp Asn Glu Cys Met Glu Ser Val Arg Asn
465                 470                 475                 480

Gly Thr Tyr Asp Tyr Pro Gln Tyr Ser Glu Glu Ser Arg Leu Asn Arg
                485                 490                 495

Glu Glu Ile Asp Gly Val Lys Leu Glu Ser Met Gly Thr Tyr Gln Ile
            500                 505                 510

Leu Ser Ile Tyr Ser Thr Val Ala Ser Ser Leu Ala Leu Ala Ile Met
        515                 520                 525
```

-continued

```
Val Ala Gly Leu Ser Phe Trp Met Cys Ser Asn Gly Ser Leu Gln Cys
    530                 535                 540

Arg Ile Cys Ile
545
```

<210> SEQ ID NO 5
<211> LENGTH: 28
<212> TYPE: DNA
<213> ORGANISM: Synthetic sequence
<220> FEATURE:
<221> NAME/KEY: misc_feature
<222> LOCATION: (1)..(28)
<223> OTHER INFORMATION: PCR primer, CVM-Asc, used to end-tailor the constitutive cassava vein mosaic virus (CsVMV) promoter on pCPH.

<400> SEQUENCE: 5
atggcgcgcc agaaggtaat tatccaag 28

<210> SEQ ID NO 6
<211> LENGTH: 24
<212> TYPE: DNA
<213> ORGANISM: Synthetic sequence
<220> FEATURE:
<221> NAME/KEY: misc_feature
<222> LOCATION: (1)..(24)
<223> OTHER INFORMATION: PCR primer, CVM-Xho, used to end-tailor the cassava vein mosaic virus (CsVMV) promoter on pCPH.

<400> SEQUENCE: 6
atctcgagcc atggtttgga tcca 24

<210> SEQ ID NO 7
<211> LENGTH: 25
<212> TYPE: DNA
<213> ORGANISM: Synthetic sequence
<220> FEATURE:
<221> NAME/KEY: misc_feature
<222> LOCATION: (1)..(25)
<223> OTHER INFORMATION: Mutagenic primer used to create a Nco I site.

<400> SEQUENCE: 7
tgccatggtg atgtgtggtc tacaa 25

<210> SEQ ID NO 8
<211> LENGTH: 23
<212> TYPE: DNA
<213> ORGANISM: Synthetic sequence
<220> FEATURE:
<221> NAME/KEY: misc_feature
<222> LOCATION: (1)..(23)
<223> OTHER INFORMATION: Forward primer complementary to the 5' region.

<400> SEQUENCE: 8
gatctgacaa gtcaagaaaa ttg 23

<210> SEQ ID NO 9
<211> LENGTH: 23
<212> TYPE: DNA
<213> ORGANISM: Synthetic sequence
<220> FEATURE:
<221> NAME/KEY: misc_feature
<222> LOCATION: (1)..(23)
<223> OTHER INFORMATION: Mutagenic primer used to create a XhoI I site.

<400> SEQUENCE: 9
agctcgagct gtgtgagtga gtg 23

<210> SEQ ID NO 10
<211> LENGTH: 1368
<212> TYPE: DNA
<213> ORGANISM: Infectious Bursal Disease Virus
<220> FEATURE:
<221> NAME/KEY: misc_feature
<222> LOCATION: (1)..(1368)
<223> OTHER INFORMATION: See Figure 14.
<220> FEATURE:
<221> NAME/KEY: misc_feature
<222> LOCATION: (1)..(1368)
<223> OTHER INFORMATION: DNA sequence of VP2 gene of Infectious Bursal Disease Virus.

<400> SEQUENCE: 10
atgaccaacc tccaagatca aactcaacag attgttccct tcatacgcag ccttctcatg 60
ccaaccactg gacctgcttc cattcctgat gacaccttgg agaagcacac tctccgctct 120
gagacctcaa cctacaactt gactgttggt gacactggct ctgggttgat tgtctttttc 180
cctgggttcc ctggctccat tgtgggtgct cactacacat tgcagtccaa tggcaactac 240
aagtttgatc aaatgctctt gactgcccag aatcttccag cctcctacaa ctattgccgt 300
cttgtgtctc gctccctcac agtgaggtcc tcaacactcc ctggtggagt gtatgcactc 360
aatggcacca tcaacgcagt gactttccaa ggaagccttt cagaattgac tgatgtgagc 420
tacaatgggt tgatgtctgc aacagccaac atcaatgaca agattgggaa tgtccttgtt 480
ggagaaggag tcaccgtcct ctcactccca acatcctatg atcttggcta tgtgagactt 540
ggtgatccca ttcctgccat aggacttgat cccaaaatgg ttgccacatg tgacagctct 600
gatcgtccaa gggtttacac catcacagca gctgatgact accaattctc ctcacagtac 660
caagctggtg gagtcaccat cacactcttc tcagccaaca tagatgccat cacaagcctc 720
agcattggtg gagaacttgt ctttcagaca tctgtccaag ggctcatcct tggtgccacc 780
atctacttga ttggctttga tggcactgct gtcatcacca gagcagtggc tgcagacaat 840
gggctcacag ctggcactga caacctcatg ccattcaaca ttgtgattcc cacctctgag 900
atcacccagc caatcacttc catcaagttg gagatagtga cctcaaagtc cggtggacaa 960
gctggtgatc agatgtcctg gtctgcatct gggagcttgg ctgtgaccat tcatggtggc 1020
aactaccccg gagccctcag acctgtgact ttggttgcct atgaacgcgt tgcaactggc 1080
tctgttgtca ctgttgctgg tgtcagcaac tttgagttga tcccaaatcc tgaacttgca 1140
aagaacttgg tcacagagta tggaaggttt gaccctggtg ccatgaacta cacaaaattg 1200
atcctctcag agagggacag acttggcatc aagactgttt ggccaaccag agagtacact 1260
gacttccgcg agtacttcat ggaggttgct gacctcaaca gccctctcaa gatagctgga 1320
gcctttggtt tcaaagacat cataagggct attcgtcgca tcgctgtt 1368

<210> SEQ ID NO 11
<211> LENGTH: 1425
<212> TYPE: DNA
<213> ORGANISM: Infectious Bursal Disease Virus
<220> FEATURE:
<221> NAME/KEY: misc_feature
<223> OTHER INFORMATION: Polynucleotide (DNA) encoding a variation of E/91 VP2 (structural protein from Infectious Bursal Disease Virus)

<400> SEQUENCE: 11
agatctgaag acaacatgac caacctccaa gatcaaactc aacagattgt tcccttcata 60
cgcagccttc tcatgccaac cactggacct gcttccattc ctgatgacac cttggagaag 120
cacactctcc gctctgagac ctcaacctac aacttgactg ttggtgacac tggctctggg 180

-continued

```
ttgattgtct ttttccctgg gttccctggc tccattgtgg gtgctcacta cacattgcag    240

tccaatggca actacaagtt tgatcaaatg ctcttgactg cccagaatct tccagcctcc    300

tacaactatt gccgtcttgt gtctcgctcc ctcacagtga ggtcctcaac actccctggt    360

ggagtgtatg cactcaatgg caccatcaac gcagtgactt tccaaggaag cctttcagaa    420

ttgactgatg tgagctacaa tgggttgatg tctgcaacag ccaacatcaa tgacaagatt    480

gggaatgtcc ttgttggaga aggagtcacc gtcctctcac tcccaacatc ctatgatctt    540

ggctatgtga gacttggtga tcccattcct gccataggac ttgatcccaa aatggttgcc    600

acatgtgaca gctctgatcg tccaagggtt tacaccatca cagcagctga tgactaccaa    660

ttctcctcac agtaccaagc tggtggagtc accatcacac tcttctcagc caacatagat    720

gccatcacaa gcctcagcat tggtggagaa cttgtctttc agacatctgt ccaagggctc    780

atccttggtg ccaccatcta cttgattggc tttgatggca ctgctgtcat caccagagca    840

gtggctgcag acaatgggct cacagctggc actgacaacc tcatgccatt caacattgtg    900

attcccacct ctgagatcac ccagccaatc acttccatca agttggagat agtgacctca    960

aagtccggtg gacaagctgg tgatcagatg tcctggtctg catctgggag cttggctgtg   1020

accattcatg gtggcaacta ccccggagcc ctcagacctg tgactttggt tgcctatgaa   1080

cgcgttgcaa ctggctctgt tgtcactgtt gctggtgtca gcaactttga gttgatccca   1140

aatcctgaac ttgcaaagaa cttggtcaca gagtatggaa ggtttgaccc tggtgccatg   1200

aactacacaa aattgatcct ctcagagagg gacagacttg gcatcaagac tgtttggcca   1260

accagagagt acactgactt ccgcgagtac ttcatggagg ttgctgacct caacagccct   1320

ctcaagatag ctggagcctt tggtttcaaa gacatcataa gggctattcg tcgcatcgct   1380

gtttgagtag ttagcttaat cacctagagc tcggtcacca gatct                   1425
```

```
<210> SEQ ID NO 12
<211> LENGTH: 456
<212> TYPE: PRT
<213> ORGANISM: Infectious Bursal Disease Virus
<220> FEATURE:
<221> NAME/KEY: misc_feature
<223> OTHER INFORMATION: Polypeptide variation of E/91 VP2 (structural
      protein from Infectious Bursal Disease Virus) encoded by SEQ ID
      NO: 11.

<400> SEQUENCE: 12

Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
```

-continued

```
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Ala Gly Gly
    210                 215                 220

Val Thr Ile Thr Leu Phe Ser Ala Asn Ile Asp Ala Ile Thr Ser Leu
225                 230                 235                 240

Ser Ile Gly Gly Glu Leu Val Phe Gln Thr Ser Val Gln Gly Leu Ile
                245                 250                 255

Leu Gly Ala Thr Ile Tyr Leu Ile Gly Phe Asp Gly Thr Ala Val Ile
            260                 265                 270

Thr Arg Ala Val Ala Ala Asp Asn Gly Leu Thr Ala Gly Thr Asp Asn
        275                 280                 285

Leu Met Pro Phe Asn Ile Val Ile Pro Thr Ser Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Ile Ala Val
    450                 455
```

<210> SEQ ID NO 13
<211> LENGTH: 42
<212> TYPE: DNA
<213> ORGANISM: Infectious Bursal Disease Virus
<220> FEATURE:
<221> NAME/KEY: misc_feature
<222> LOCATION: (1)..(42)
<223> OTHER INFORMATION: DNA sequence encoding translation termination ("Stop") codons, used to terminate translation of inadvertant open reading frames following DNA integration during transformation (includes Sac I BstE II, and Bgl II restriction enzyme recogniton sites).

<400> SEQUENCE: 13

```
tgagtagtta gcttaatcac ctagagctcg gtcaccagat ct                  42
```